(12) United States Patent
Papisov

(10) Patent No.: US 8,383,758 B2
(45) Date of Patent: *Feb. 26, 2013

(54) BIODEGRADABLE POLYKETAL POLYMERS AND METHODS FOR THEIR FORMATION AND USE

(75) Inventor: Mikhail I. Papisov, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/093,951

(22) Filed: Apr. 26, 2011

(65) Prior Publication Data

US 2011/0275700 A1 Nov. 10, 2011

Related U.S. Application Data

(62) Division of application No. 12/620,855, filed on Nov. 18, 2009, now Pat. No. 7,951,898, which is a division of application No. 10/501,565, filed as application No. PCT/US03/01017 on Jan. 14, 2003, now Pat. No. 7,838,619.

(60) Provisional application No. 60/348,333, filed on Jan. 14, 2002.

(51) Int. Cl.
*C08G 16/00* (2006.01)
*C08G 65/00* (2006.01)

(52) U.S. Cl. .................................. 528/220; 528/425

(58) Field of Classification Search ............... 528/220, 528/425
See application file for complete search history.

(56) References Cited

U.S. PATENT DOCUMENTS 3,691,090 A 9/1972 Kitajima et al.
(Continued)

FOREIGN PATENT DOCUMENTS

EP 0280474 A2 8/1988
EP 0325270 A2 7/1989
(Continued)

OTHER PUBLICATIONS

Bendele et al., Short Communication: Renal Tubular Vacuolation in Animals Treated with Polyethylene-Glycol-Conjugated Proteins, *Toxicological Sciences*, 42: 152-157, 1997.
(Continued)

*Primary Examiner* — Duc Truong
(74) *Attorney, Agent, or Firm* — Choate, Hall & Stewart LLP; Brenda Herschbach Jarrell; Kristen C. Buteau

(57) ABSTRACT

The present invention relates to biodegradable biocompatible polyketals, methods for their preparation, and methods for treating animals by administration of biodegradable biocompatible polyketals. In one aspect, a method for forming the biodegradable biocompatible polyketals comprises combining a glycol-specific oxidizing agent with a polysaccharide to form an aldehyde intermediate, which is combined with a reducing agent to form the biodegradable biocompatible polyketal. The resultant biodegradable biocompatible polyketals can be chemically modified to incorporate additional hydrophilic moieties. A method for treating animals includes the administration of the biodegradable biocompatible polyketal in which biologically active compounds or diagnostic labels can be disposed.

The present invention also relates to chiral polyketals, methods for their preparation, and methods for use in chromatographic applications, specifically in chiral separations. A method for forming the chiral polyketals comprises combining a glycol-specific oxidizing agent with a polysaccharide to form an aldehyde intermediate, which is combined with a suitable reagent to form the chiral polyketal. A method for use in chiral separations includes the incorporation of the chiral polyketals in the mobile phase during a chromatographic separation, or into chiral stationary phases such as gels.

The present invention further relates to chiral polyketals as a source for chiral compounds, and methods for generating such chiral compounds.

12 Claims, 4 Drawing Sheets

U.S. PATENT DOCUMENTS

| | | | |
|---|---|---|---|
| 4,247,611 | A | 1/1981 | Sander et al. |
| 4,374,953 | A | 2/1983 | Chou et al. |
| 4,389,330 | A | 6/1983 | Tice et al. |
| 4,882,397 | A | 11/1989 | Kelsey |
| 5,075,222 | A | 12/1991 | Hannum et al. |
| 5,574,127 | A | 11/1996 | Sau |
| 5,582,172 | A | 12/1996 | Papisov et al. |
| 5,612,037 | A | 3/1997 | Huebner et al. |
| 5,624,803 | A | 4/1997 | Noonberg et al. |
| 5,811,510 | A | 9/1998 | Papisov |
| 5,817,343 | A | 10/1998 | Burke |
| 5,824,784 | A | 10/1998 | Kinstler et al. |
| 5,830,730 | A | 11/1998 | German et al. |
| 5,863,990 | A | 1/1999 | Papisov |
| 5,932,462 | A | 8/1999 | Harris et al. |
| 5,935,599 | A | 8/1999 | Dadey |
| 5,958,398 | A | 9/1999 | Papisov |
| 6,048,837 | A | 4/2000 | Friedman et al. |
| 6,057,431 | A | 5/2000 | Ishihara et al. |
| 6,262,107 | B1 | 7/2001 | Li et al. |
| 6,294,170 | B1 | 9/2001 | Boone et al. |
| 6,312,727 | B1 | 11/2001 | Schacht et al. |
| 6,312,732 | B1 | 11/2001 | Sokoll et al. |
| 6,822,086 | B1 | 11/2004 | Papisov |
| 7,160,924 | B2 | 1/2007 | Kinstler et al. |
| 7,270,808 | B2 | 9/2007 | Cheng et al. |
| 7,838,619 | B2 * | 11/2010 | Papisov ............ 528/220 |
| 7,951,898 | B2 * | 5/2011 | Papisov ............ 528/220 |
| 2002/0082362 | A1 | 6/2002 | Brocchini et al. |
| 2004/0105840 | A1 | 6/2004 | Kinstler et al. |
| 2005/0169968 | A1 | 8/2005 | Elmaleh et al. |
| 2006/0019911 | A1 | 1/2006 | Papisov |
| 2006/0058513 | A1 | 3/2006 | Papisov et al. |
| 2006/0069230 | A1 | 3/2006 | Papisov |
| 2007/0190018 | A1 | 8/2007 | Papisov |
| 2008/0019940 | A1 | 1/2008 | Papisov |
| 2011/0059010 | A1 | 3/2011 | Papisov et al. |

FOREIGN PATENT DOCUMENTS

| | | |
|---|---|---|
| WO | WO-9605309 A2 | 2/1996 |
| WO | WO-9640912 A1 | 12/1996 |
| WO | WO-9930561 A1 | 6/1999 |
| WO | WO-0078355 A2 | 12/2000 |
| WO | WO-0107486 A1 | 2/2001 |
| WO | WO-0110468 A2 | 2/2001 |
| WO | WO-03059988 A2 | 7/2003 |

OTHER PUBLICATIONS

Bruneel D. et al. "Chemical modification of pullulan: 3. Succinoylation" *Polymer, Elsevier Science Publishers B.V*, GB, vol. 35, No. 12: 2656-2658, 1994.

Cervigni S. et al. "Synthesis of Glycopeptides and Lipopeptides by Chemoselective Ligation" *Angew. Chem. Int. Ed. Egl.* 35, No. 11: 1230-1232, 1996.

Conover, C. et al. Physiological Effect of Polyethylene Glycol Conjugation on Stroma-Free Bovine Hemoglobin in the Conscious Dog After Partial Exchange Transfusion, *Artificial Organs*, vol. 21, No. 5: 369-378, 1997.

Duncan, R. Polymer-Drug Conjugates. In: *Handbook of Anticancer Drug Development*, D. Budman, H. Calvert, and E. Rowinsky (Eds.), Lippincott, Williams & Wilkins Philadelphia, pp. 239-260, 2003.

Endo et al. Nature of Linkage and Mode of Action of Methotrexate Conjugated with Antitumor Antibodies: Implications for Future Preparation of Conjugates. *Cancer Research* 48: 3330-3335, Jun. 15, 1988.

Feng et al. Synthesis and Evaluation of Water-Soluble Paclitaxel Prodrugs. *Bioorganic & Medicinal Chemistry Letters* 12: 3301-3303, 2002.

Gao Q. et al. "Drug-induced DNA repair: X-ray structure of a DNA-ditercalinium complex". Proc. Natl. Acad. Sci. USA vol. 88: 2422-2426, Mar. 1991.

Hermanson G. *Bioconjugate Techniques*, pp. 548-569, 1996.

Jordan, Craig V. Tamoxifen: A Most Unlikely Pioneering Medicine. *Nature Reviews*. vol. 2: 205-213, 2003.

Matysiak S. "Acetal Oligonucleotide Conjugates in Antisense Strategy" *Nucleosides & Nucleotides*, 16(5&6): pp. 855-861, 1997.

Papisov M.I. et al. "Semisynthetic Hydrophilic Polyals" *Biomacromolecules*, vol. 6: 2659-2670, 2005.

Tomlinson et al. Polyacetal-Doxorubicin Conjugates Designed for pH-Dependent Degradation. *Bioconjugate Chem.*, 14: 1096-1106, 2003.

Zalipsky et al. Attachment of Drugs to Polyethylene Glycols. *Eur. Polym. J.*, 19(12): 1177-1183, 1983.

Papisov, M et al. Fully biodegradable hydrophilic polyals (polyacetals and polyketals). 29th Int. Symp. On Controlled Release of Bioactive Materials, 2002, Seoul, Korea. *Controlled Release Society*, Deerfield, IL, 2002; paper # 465.

Papisov, M. Theoretical considerations of RES-avoiding liposomes. *Adv. Drug Delivery Rev.*, 32, 119-138, 1998.

Papisov, M. Acyclic polyacetals from polysaccharides. (Biopolymers from polysaccharides and agroproteins), *ACS Symposium Series*, 2001, 786: 301-314.

Papisov, M. et al. A long-circulating polymer with hydrolizable main chain. 23-rd International Symposium on Controlled Release of Bioactive Materials, Kyoto, Japan, 1996; *Controlled Release Society*, Deerfield, IL, 1996, 107-108.

Papisov, M. et al. Fully biodegradable hydrophilic polyacetals for macromolecular radiopharmaceuticals. *49th Annual Meeting of the Society of Nuclear Medicine*, Los Angeles, CA, 2002. J. Nuc. Med. 43:5 (abstract) p. 377P, 2002.

Papisov, M. et al. Hydrophilic Polyals: Biomimetic Biodegradable Stealth Materials for Pharmacology and Bioengineering. Proceedings of 226th *Natl. Meeting of American Chemical Society*, New York, NY, 2003.

Papisov, MI et al. Model cooperative (multivalent) vectors for drug targeting. 25th Int. Symp. on Controlled Release of Bioactive Materials, 1998, Las Vegas, Nevada, USA; *Controlled Release Society*, Deerfield, IL, 1998, 170-171.

Papisov, MI. Modeling in vivo transfer of long-circulating polymers (two classes of long circulating polymers and factors affecting their transfer in vivo). *Adv. Drug Delivery Rev.*, Special issue on long circulating drugs and drug carriers, 16:127-139, 1995.

Yurkovetskiy, A. et al. Biodegradable polyal carriers for protein modification. 29th Int. Symp. on Controlled Release of Bioactive Materials, 2002, Seoul, Korea. *Controlled Release Society*, Deerfield, IL, 2002; paper # 357.

Yurkovetskiy, A. et al. Biodegradable polyals for protein modification. *Controlled Release Society's Winter Symposium*, Salt Lake City, Utah, 2003.

Yurkovetsky, A. et al., Fully Degradable Hydrophilic Polyals for Protein Modification. *Biomacromolecules*, 6: 2648-2658, 2005.

Edwards, et al., "Large Porous Particles for Pulmonary Drug Delivery", *Science*, 276: 1868-1872, 1997.

Fidler, et al., "The biology of cancer invasion and metastasis", *Adv. Cancer Res.*, 28: 149-250, 1987.

Horwitz et al., "Taxol: Mechanisms of Action and Resistance", *J. Natl. Cancer Inst.* Monographs No. 15: 55-61, 1993.

International Search Report for PCT/US03/01017, mailed Sep. 30, 2003.

Maeda, et al., Tumoritropic and Lymphotropic Principles of Macromolecular Drugs, *Critical Review in Therapeutic Drug Carrier Systems*, 6(3): 193-210, 1989.

Mathiowitz et al., "Biologically erodable microspheres as potential oral drug delivery systems", *Nature*, 386: 410-414, 1997.

Putney, et al., "Improving protein therapeutics with sustained-release formulations", *Nature Biotechnology* 16: 153-157, 1998.

Reynolds, T., "Polymers help guide cancer drugs to tumor targets-and keep them there", *J. Natl. Cancer Institute*, 87(21): 1582-1584, 1995.

* cited by examiner

BIODEGRADABLE POLYKETAL POLYMERS AND METHODS FOR THEIR FORMATION AND USE

PRIORITY CLAIM

The present application is a divisional application of and claims priority to application Ser. No. 12/620,855, filed Nov. 18, 2009, now U.S. Pat. No. 7,951,898; which is a divisional application of application Ser. No. 10/501,565, filed Jul. 14, 2004, now U.S. Pat. No. 7,838,619, issued Nov. 23, 2010; which claims the benefit under 35 U.S.C. §371 of International Application No.: PCT/US03/01017 (International Publication No. WO 03/59988), filed Jan. 14, 2003, which claims priority to U.S. Patent Application No. 60/348,333, filed Jan. 14, 2002, the entire contents of each of the above applications are incorporated herein by reference.

GOVERNMENT FUNDING

The present invention was made with U.S. government support under grant R21RR14221 awarded by the National Center for Research Resources of the National Institutes of Health. Accordingly, the United States Government has certain rights in this invention.

BACKGROUND OF THE INVENTION

Biodegradable Polymers—Biomedical Devices and Drug Delivery Systems

Traditionally, pharmaceuticals have primarily consisted of small molecules that are dispensed orally (as solid pills and liquids) or as injectables. Over the past three decades, however, sustained release formulations (i.e., compositions that control the rate of drug delivery and allows delivery of the therapeutic agent at the site where it is needed) have become increasingly common and complex. Nevertheless, many questions and challenges regarding the development of new treatments as well as the mechanisms with which to administer them remain to be addressed.

Although considerable research efforts in this area have led to significant advances, drug delivery methods/systems that have been developed over the years and are currently used, still exhibit specific problems that require some investigating. For example, many drugs exhibit limited or otherwise reduced potencies and therapeutic effects because of they are generally subject to partial degradation before they reach a desired target in the body. Once administered, sustained release medications deliver treatment continuously, e.g. for days or weeks, rather than for a short period of time (hours or minutes). Furthermore, orally administered therapeutics are generally preferable over injectable medications, which are often more expensive and are more challenging to administer, and thus it would be highly desirable if injectable medications could simply be dosed orally. However, this goal cannot be achieved until methods are developed to safely shepherd drugs through tissue barriers, such as epithelial or dermal barriers, or specific areas of the body, such as the stomach, where low pH can degrade or destroy a medication, or through an area where healthy tissue might be adversely affected.

One objective in the field of drug delivery systems, therefore, is to deliver medications intact to specifically targeted areas of the body through a system that can control the rate and time of administration of the therapeutic agent by means of either a physiological or chemical trigger. Over the past decade, materials such as polymeric microspheres, polymer micelles, soluble polymers and hydrogel-type materials have been shown to be effective in enhancing drug targeting specificity, lowering systemic drug toxicity, improving treatment absorption rates, and providing protection for pharmaceuticals against biochemical degradation, and thus have shown great potential for use in biomedical applications, particularly as components of drug delivery devices.

The design and engineering of biomedical polymers (e.g., polymers for use under physiological conditions) are generally subject to specific and stringent requirements. In particular, such polymeric materials must be compatible with the biological milieu in which they will be used, which often means that they show certain characteristics of hydrophilicity. They also have to demonstrate adequate biodegradability (i.e., they degrade to low molecular weight species. The polymer fragments are in turn metabolized in the body or excreted, leaving no trace).

Biodegradability is typically accomplished by synthesizing or using polymers that have hydrolytically unstable linkages in the backbone. The most common chemical functional groups with this characteristic are esters, anhydrides, orthoesters, and amides. Chemical hydrolysis of the hydrolytically unstable backbone is the prevailing mechanism for the polymer's degradation. Biodegradable polymers can be either natural or synthetic. Synthetic polymers commonly used in medical applications and biomedical research include polyethyleneglycol (pharmacokinetics and immune response modifier), polyvinyl alcohol (drug carrier), and poly(hydroxypropylmetacrylamide) (drug carrier). In addition, natural polymers are also used in biomedical applications. For instance, dextran, hydroxyethylstarch, albumin and partially hydrolyzed proteins find use in applications ranging from plasma substitute, to radiopharmaceutical to parenteral nutrition. In general, synthetic polymers may offer greater advantages than natural materials in that they can be tailored to give a wider range of properties and more predictable lot-to-lot uniformity than can materials from natural sources. Synthetic polymers also represent a more reliable source of raw materials, one free from concerns of infection or immunogenicity. Methods of preparing polymeric materials are well known in the art. However, synthetic methods that successfully lead to the preparation of polymeric materials that exhibit adequate biodegradability, biocompatibility, hydrophilicity and minimal toxicity for biomedical use are scarce. The restricted number and variety of biopolymers currently available attest to this.

Therefore a need exists in the biomedical field for non-toxic, biodegradable, biocompatible, hydrophilic polymers, which overcome or minimize the above-referenced problems. Such polymers would find use in several applications, including components for biomedical preparations, pharmaceutical formulations, medical devices, implants, and the packaging/delivery of therapeutic, diagnostic and prophylactic agents.

Chromatographic Applications:

Another important aspect pertaining to polymeric materials is that of chiral polymers for use as chiral chromatographic phases for the separation of stereoisomers.

The separation of mixtures of stereoisomers (enantiomers or diastereomers) into individual optical isomers is one of the most challenging problems in analytical chemistry, reflecting practical considerations important in many areas of science, particularly the pharmaceutical and agricultural industries.

For example, the pharmaceutically active site of many drugs is "chiral," meaning that the active site is not identical to a mirror image of the site. However, many pharmaceutical formulations marketed today are racemic mixtures of the desired compound and its "mirror image." The separation of racemates of active compounds into their optical antipodes has gained increasing importance in recent years, since it has been demonstrated that the enantiomers of a chiral active compound often differ significantly in their actions and side-effects. One optical form (or enantiomer) of a racemic mixture may be medicinally useful, while the other optical form may be inert or even harmful, as has been reported to be the case for thalidomide.

Accordingly, chiral drugs are now extensively evaluated prior to large scale manufacturing, both to examine their efficacy, and to minimize undesirable effects attributable to one enantiomer or to the interaction of enantiomers in a racemic mixture. The United States Food and Drug Administration has recently issued new regulations governing the marketing of chiral drugs.

Early chiral separation methods used naturally occurring chiral species in otherwise standard separation protocols. For example, natural chiral polymeric adsorbents such as cellulose, other polysaccharides, and wool were used as early as the 1920's. Later strategies used other proteins and naturally occurring chiral materials. These early strategies gave some degree of success. However, the poor mechanical and chromatographic properties of naturally occurring materials often complicated the separations. Although naturally occurring chiral materials continue to be used for chiral separations, efforts have increasingly turned to synthesizing chiral materials having better mechanical and chromatographic properties.

Separating optical isomers often requires considerable time, effort, and expense, even when state-of-the-art chiral separation techniques are used. There is a continuing and growing need for improved chiral separation techniques, as well as new compositions and methods useful in chiral separations of enantiomeric mixtures.

Chiral Compounds Synthesis:

Many biologically active molecules are optically active (chiral), and usually the biological activity can vary greatly depending on the optical purity of the molecule. As mentioned above, in pharmaceutical applications, the optical activity can have a great impact the activity of the drug, and thus on its marketability. Much research activity has been focused on the development of technologies allowing access to pure enantiomers.

Typically, pure enantiomers may be obtained by one of three methods: (1) chiral synthesis, (2) achiral synthesis followed by indirect resolution, or (3) achiral synthesis followed by resolution by chromatography.

The ability to build optical activity into the molecule as it is being synthesized is an important asset, and significant research efforts have been devoted to the development of enantioselective syntheses in recent years. Chiral synthesis requires a chiral starting point, it is complex and requires care to avoid racemization. The chiral purity must be monitored throughout the synthesis. The advantages are apparent in the long term due to the lack of wastage of the unwanted enantiomer and the ability to scale up the reaction to production size. However, enantioselective syntheses are often difficult, time consuming, and require chiral reagents that are generally expensive.

Chiral compounds may also be obtained from achiral synthesis (which is generally faster, more accessible and significantly less costly than a chiral synthesis), by subjecting the achiral material to indirect resolution methods such as crystallization, enzymatic reaction (which selectively destroys the unwanted isomer), or diastereoisomeric resolution (formation of the diastereomer followed by crystallization). The major drawback with these methods is that they all require a chiral selector with a very high degree of enantioselectivity, which implies that it must be very pure itself. An impure selector will result in a loss of purity and yield of the enantiomers resolved.

Alternatively, the separation of enantiomers may be achieved by chromatographic techniques, either by using chiral stationary phases (CSP) or chiral mobile phase additives (CMPA) to perform the chromatographic separation, or by forming a diastereomeric derivative suitable for chromatographic separation. Nevertheless, these methods suffer from the same disadvantages as the methods outlined above: they are time consuming, require chiral reagents/stationary phase that are generally expensive, and the chromatography can also be difficult and may take considerable development.

Therefore, a need exists for novel materials and methods that would effectively and inexpensively allow access to useful chiral compounds.

SUMMARY OF THE INVENTION

The present invention discloses a polymeric material that is biodegradable, biocompatible and exhibits little toxicity and/or bioadhesivity in vivo, and contains hydrophilic and/or pharmaceutically useful groups. Specifically, the polymeric material is a polyketal.

In one aspect, the invention encompasses biodegradable biocompatible polyketals comprising repeat structural units, wherein substantially all the structural units comprise (i) at least one ketal group wherein at least one ketal oxygen atom is within the polymer main chain; and (ii) at least one hydrophilic group or pharmaceutically useful group. In another aspect of the invention, at least a subset of the repeat structural units have the following chemical structure:

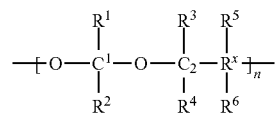

wherein each occurrence of $R^1$ and $R^2$ is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ is either hydrophilic or pharmaceutically useful.

In yet another aspect, the biodegradable biocompatible polyketals of the invention comprise repeat structural units having the following chemical structure:

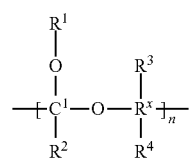

wherein each occurrence of $R^2$ is a biocompatible group and includes a carbon atom covalently attached to $C^1$; $R^x$ includes a carbon atom covalently attached to $C^1$; n is an integer; each occurrence of $R^1$, $R^3$ and $R^4$ is a biocompatible group and is independently hydrogen or an organic moiety;

and for each occurrence of the bracketed structure n, at least one of $R^1$, $R^2$, $R^3$ and $R^4$ is either hydrophilic or pharmaceutically useful.

In the above structures, n refers to the number of ketal moieties in the molecule, wherein n is an integer larger than 1. There is generally no requirement that all ketal moieties be connected to each other directly, or that the molecule be strictly regular and consist only of the repeat structures depicted above. For example, the bracketed structures may not necessarily be positioned in a head-to-tail fashion throughout the polymeric chain. Irregularities may exist in the polymer backbone, whereby, for example, a number of monomeric units differ from the general structures depicted above. In addition, where the polyketals of the invention are prepared from co-polymerization of at least two monomers or from a polysaccharide comprising more than one type of saccharide moiety, the group of substituents ($R^1$-$R^6$) in each structural unit of the polymeric chain may not be identical throughout the polymer and they may vary from one structural unit to the next. For the purpose of the invention, it is to be understood that the substitutents $R^1$-$R^6$ as used herein may be the same or different throughout the polymer structure. In addition, the structures of the polyketals of the invention are not limited to that depicted herein. The invention broadly encompasses polyketals structures wherein at least one ketal oxygen belongs to the main chain, and wherein substantially all monomeric units comprise at least one hydrophilic group or a pharmaceutically useful group.

In a further aspect, the invention provides a method for forming a biodegradable polyketal which includes combining an effective amount of a glycol-specific oxidizing agent with a polysaccharide containing ketal groups within the main chain to open or laterally cleave the carbohydrate rings and form an acyclic aldehyde-substituted polyketal. The aldehyde-substituted polyketal can then be utilized without further modification or can be reacted with a suitable reagent to derivatize the aldehyde moieties into other suitable groups, thus forming a biodegradable polyketal with the desired chemical functionality and/or physicochemical properties.

In another aspect of the invention, a method for forming biodegradable polyketals includes polymerization or copolymerization of suitable monomers, such as substituted 1,3-dioxolanes; ketones and polyols (or suitable derivatives thereof); divinyl-substituted ketals and polyols, etc. For example, the method can include reacting a suitable initiator with a compound having the chemical structure:

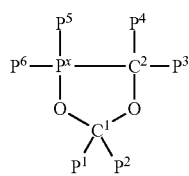

The reaction results in the formation of a polymer comprising the chemical structure:

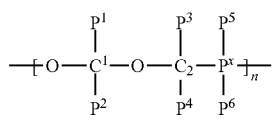

wherein each occurrence of $P^1$ and $P^2$ includes a carbon atom covalently attached to $C^1$ and is independently an organic moiety or a protected organic moiety; $P^x$ includes a carbon atom covalently attached to $C^2$; n is an integer; each occurrence of $P^3$, $P^4$, $P^5$ and $P^6$ is independently hydrogen, an organic moiety or a protected organic moiety. For each occurrence of the bracketed structure n, at least one of $P^1$, $P^2$, $P^3$, $P^4$, $P^5$ and $P^6$ is either a protected hydrophilic group, or a pharmaceutically useful group. In a preferred embodiment, $P^1$, $P^2$, $P^3$, $P^4$, $P^5$ and $P^6$ do not prevent polymerization. In one embodiment, the protected hydrophilic groups or protected organic moieties of the polymer intermediate are deprotected and optionally derivatized, thereby forming the polyketal comprising the structure:

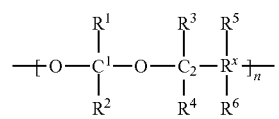

wherein each occurrence of $R^1$ and $R^2$ is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and, for each occurrence of the bracketed structure n, at least one of $R^1$, $R^2$, $R^3$, $R^4$, $R^5$ and $R^6$ is either hydrophilic or pharmaceutically useful. Alternatively, other ring opening techniques can be employed or developed, for example employing appropriate catalysts and resulting in the formation of polyketals comprising unsaturated linkages within the main chain. The latter can be further transformed into single bonds using appropriate reagents.

The present invention offers many advantages. For example, the reactants employed to form the biodegradable biocompatible polyketals are either readily available or can be synthesized using methods generally known in the art. Polysaccharides used for lateral cleavage with conversion to acyclic polyketals are available from plants or can be manufactured using methods known and practiced in biotechnology. Furthermore, the resultant biodegradable biocompatible polyketals can be modified to obtain products with desirable properties, such as by modification with additional hydrophilic or hydrophobic moieties, pharmaceutically useful groups, biologically active molecules or diagnostic labels. Also, the biodegradable biocompatible polyketal can be used as pharmaceutical excipients or components thereof.

The biodegradable biocompatible polyketals of the present invention are built of essentially acyclic structures and therefore are distinct from naturally-occurring polysaccharides. For example, in certain embodiments, the polysaccharide ring structure is opened or laterally cleaved during the synthesis of the biodegradable biocompatible polyketals and is essentially absent from the polymer structure. Furthermore, without wishing to be bound by any particular theory, we propose that the biodegradable biocompatible polyketals of the present invention may have a higher degree of biocompatibility relative to the polysaccharides from which they are derived since they generally do not contain cyclic carbohydrates—which are potentially receptor recognizable or immunogenic. The presence or absence of cyclic structures can be established by Nuclear Magnetic Resonance (NMR) spectroscopy.

In another aspect, the invention provides methods for using the polyketals in biomedical applications, primarily (nut not exclusively) in the fields of pharmacology, bioengineering, wound healing, and dermatology/cosmetics. In particular, medical applications for the biocompatible biodegradable polymers of the invention include main or accessory materials for the following: tablet coatings, plasma substitutes, gels, contact lenses, surgical implants, systems for controlled drug release, as ingredients of eyedrops, wound closure applications (sutures, staples), orthopedic fixation devices (pins, rods, screws, tacks, ligaments), dental applications (guided tissue regeneration), cardiovascular applications (stents, grafts), intestinal applications (anastomosis rings), implantable drug delivery devices and matrices, bioresorbable templates for tissue engineering, and long circulating and targeted drugs.

In one aspect, the invention provides a method for treating an animal, which method comprises administering the biodegradable biocompatible polyketal to the animal Pharmaceutically useful components, such as biologically active compounds or diagnostic labels, can be incorporated into a solution or a gel which includes the biodegradable biocompatible polyketal of the invention. Mixtures of such components can be disposed within the solution or gel. For example, pharmaceutical components can be linked to the polyketal by a chemical bond or dispersed throughout the biocompatible biodegradable polyketal solution or gel.

In another aspect, the present invention provides chiral polyketals, methods of preparation and methods of use thereof. For example, chiral polyketals in accordance with the invention may find use in chromatographic applications, specifically in chiral separations. Such chiral polyketals can be incorporated in the mobile phase during a chromatographic separation, or they could instead be incorporated into chiral stationary phases such as gels, wall coatings, and packed columns and capillaries through means known in the art.

A further aspect of the invention provides methods of using the chiral polyketals of the present invention as a valuable alternative source for chiral compounds. For instance, depolymerization (e.g., hydrolysis, enzymatic degradation or acidic treatment in organic media) of the chiral polyketals of the present invention will result in the monomeric components ketones and alcohols, or in hydroxyketones, which are chiral moieties, and can thus be used for enantioselective syntheses. Certain functional groups of the polyketals may have to be protected before initiating depolymerization, using methods known in the art in order to generate final products with the desired functionality.

Definitions

"Biocompatible": The term "biocompatible", as used herein is intended to describe compounds that exert minimal destructive or host response effects while in contact with body fluids or living cells or tissues. Thus a biocompatible group, as used herein, refers to an aliphatic, alicyclic, heteroaliphatic, heteroalicyclic, aryl or heteroaryl moiety, which falls within the definition of the term biocompatible, as defined above and herein. The term "Biocompatibility" as used herein, is also taken to mean minimal interactions with recognition proteins, e.g., naturally occurring antibodies, cell proteins, cells and other components of biological systems. However, substances and functional groups specifically intended to cause the above effects, e.g., drugs and prodrugs, are considered to be biocompatible. Preferably, compounds are "biocompatible" if their addition to normal cells in vitro, at concentrations similar to the intended in vivo concentration, results in less than or equal to 5% cell death during the time equivalent to the half-life of the compound in vivo (e.g., the period of time required for 50% of the compound administered in vivo to be eliminated/cleared), and their administration in vivo induces minimal inflammation, foreign body reaction, immunotoxicity, chemical toxicity or other such adverse effects. In the above sentence, the term "normal cells" refers to cells that are not intended to be destroyed by the compound being tested. For example, non-transformed cells should be used for testing biocompatibility of antineoplastic compounds.

"Biodegradable": As used herein, "biodegradable" polymers are polymers that are susceptible to biological processing in vivo. As used herein, "biodegradable" compounds are those that, when taken up by cells, can be broken down by the lysosomal or other chemical machinery or by hydrolysis into components that the cells can either reuse or dispose of without significant toxic effect on the cells. The degradation fragments preferably induce no or little organ or cell overload or pathological processes caused by such overload or other adverse effects in vivo. Examples of biodegradation processes include enzymatic and non-enzymatic hydrolysis, oxidation and reduction. Suitable conditions for non-enzymatic hydrolysis, for example, include exposure of the biodegradable polyketals to water at a temperature and a pH of lysosomal intracellular compartment. Biodegradation of polyketals of the present invention can also be enhanced extracellularly, e.g. in low pH regions of the animal body, e.g. an inflamed area, in the close vicinity of activated macrophages or other cells releasing degradation facilitating factors. In certain preferred embodiments, the effective size of the polymer at pH~7.5 does not detectably change over 1 to 7 days, and remains within 50% of the original polymer size for at least several weeks. At pH~5, on the other hand, the polymer preferably detectably degrades over 1 to 5 days, and is completely transformed into low molecular weight fragments within a two-week to several-month time frame. Polymer integrity in such tests can be measured, for example, by size exclusion HPLC. Although faster degradation may be in some cases preferable, in general it may be more desirable that the polymer degrades in cells with the rate that does not exceed the rate of metabolization or excretion of polymer fragments by the cells. In preferred embodiments, the polymers and polymer biodegradation byproducts are biocompatible.

"Hydrophilic": The term "hydrophilic" as it relates to substituents on the polymer monomeric units does not essentially differ from the common meaning of this term in the art, and denotes organic moieties which contain ionizable, polar, or polarizable atoms, or which otherwise may be solvated by water molecules. Thus a hydrophilic group, as used herein, refers to an aliphatic, alicyclic, heteroaliphatic, heteroalicyclic, aryl or heteroaryl moiety, which falls within the definition of the term hydrophilic, as defined above. Examples of particular hydrophilic organic moieties which are suitable include, without limitation, aliphatic or heteroaliphatic groups comprising a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters and polythioesters. In preferred embodiments of the present invention, at least one of the polymer monomeric units include a carboxyl group (COOH), an aldehyde group (CHO), a methylol ($CH_2OH$) or a glycol (for example, CHOH—$CH_2$OH or CH—($CH_2$OH)$_2$).

"Hydrophilic": The term "hydrophilic" as it relates to the polymers of the invention generally does not differ from usage of this term in the art, and denotes polymers comprising hydrophilic functional groups as defined above. In a preferred embodiment, hydrophilic polymer is a water-soluble polymer. Hydrophilicity of the polymer can be directly measured through determination of hydration energy, or determined through investigation between two liquid phases, or by chromatography on solid phases with known hydrophobicity, such as, for example, C4 or C18.

"Biomolecules": The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) which belong to classes of chemical compounds, whether naturally-occurring or artificially created (e.g., by synthetic or recombinant methods), that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Physiological conditions": The phrase "physiological conditions", as used herein, relates to the range of chemical (e.g., pH, ionic strength) and biochemical (e.g., enzyme concentrations) conditions likely to be encountered in the extracellular fluids of living tissues. For most normal tissues, the physiological pH ranges from about 7.0 to 7.4. Circulating blood plasma and normal interstitial liquid represent typical examples of normal physiological conditions.

"Polysaccharide", "carbohydrate" or "oligosaccharide": The terms "polysaccharide", "carbohydrate", or "oligosaccharide" are known in the art and refer, generally, to substances having chemical formula $(CH_2O)_n$, where generally $n>2$, and their derivatives. Carbohydrates are polyhydroxyaldehydes or polyhydroxyketones, or change to such substances on simple chemical transformations, such as hydrolysis, oxidation or reduction. Typically, carbohydrates are present in the form of cyclic acetals or ketals (such as, glucose or fructose). Said cyclic units (monosaccharides) may be connected to each other to form molecules with few (oligosaccharides) or several (polysaccharides) monosaccharide units. Often, carbohydrates with well defined number, types and positioning of monosaccharide units are called oligosaccharides, whereas carbohydrates consisting of mixtures of molecules of variable numbers and/or positioning of monosaccharide units are called polysaccharides. The terms "polysaccharide", "carbohydrate", and "oligosaccharide", are used herein interchangeably. A polysaccharide may include natural sugars (e.g., glucose, fructose, galactose, mannose, arabinose, ribose, and xylose) and/or modified sugars (e.g., 2'-fluororibose, 2'-deoxyribose, and hexose).

"Small molecule": As used herein, the term "small molecule" refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. Typically, small molecules have a molecular weight of less than about 1500 g/mol. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered suitable for use with the present hydrophilic polymers.

Classes of small molecule drugs that can be used in the practice of the present invention include, but are not limited to, vitamins, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents. Many large molecules are also drugs.

A more complete, although not exhaustive, listing of classes and specific drugs suitable for use in the present invention may be found in "Pharmaceutical Substances: Syntheses, Patents, Applications" by Axel Kleemann and Jurgen Engel, Thieme Medical Publishing, 1999 and the "Merck Index: An Encyclopedia of Chemicals, Drugs, and Biologicals", Edited by Susan Budavari et al., CRC Press, 1996, both of which are incorporated herein by reference.

"Pharmaceutically useful group or entity": As used herein, the term Pharmaceutically useful group or entity refers to a compound or fragment thereof, or an organic moiety which, when associated with the polyketal polymers of the present invention, can exert some biological or diagnostic function or activity when administered to a subject, or enhance the therapeutic, diagnostic or preventive properties of the polyketal in biomedical applications, or improve safety, alter biodegradation or excretion, or is detectable. Examples of suitable pharmaceutically useful groups or entities include hydrophilicity/hydrophobicity modifiers, pharmacokinetic modifiers, biologically active modifiers, detectable modifiers. A modifier can have one or more pharmaceutical functions, e.g., biological activity and pharmacokinetics modification. Pharmacokinetics modifiers can include, for example, antibodies, antigens, receptor ligands, hydrophilic, hydrophobic or charged groups. Biologically active modifiers include, for example, therapeutic drugs and prodrugs, antigens, immunomodulators. Detectable modifiers include diagnostic labels, such as radioactive, fluorescent, paramagnetic, superparamagnetic, ferromagnetic, X-ray modulating, X-ray-opaque, ultrasound-reflective, and other substances detectable by one of available clinical or laboratory methods, e.g., scintigraphy, NMR spectroscopy, MRI, X-ray tomography, sonotomography, photoimaging, radioimmunoassay. Modifiers can be small molecules or macromolecules, and can belong to any chemical or pharmaceutical class, e.g., nucleotides, chemotherapeutic agents, antibacterial agents, antiviral agents, immunomodulators, hormones or analogs thereof, enzymes, inhibitors, alkaloids and therapeutic radionuclides. Viral and non-viral gene vectors are considered to be a pharmaceutically useful entity or group. For the purpose of this invention, the group of chemotherapeutic agents include, but is not limited to, topoisomerase I and II inhibitors, alkylating agents, anthracyclines, doxorubicin, cisplatin, carboplatin, vincristine, mitromycine, taxol, camptothecin, antisense oligonucleotides, ribozymes, and dactinomycines.

"Macromolecule": As used herein, the term macromolecule refers to molecules, whether naturally-occurring or artificially created (e.g., via chemical synthesis) that have a relatively high molecular weight, generally above 1500 g/mole Preferred macromolecules are biologically active in that they exert a biological function in animals, preferably mammals, more preferably humans. Examples of macromolecules include proteins, enzymes, growth factors, cytokines, peptides, polypeptides, polylysine, proteins, lipids, polyelectrolytes, immunoglobulins, DNA, RNA, ribozymes, plasmids, and lectins. For the purpose of this invention, supramolecular constructs such as viruses and protein associates (e.g., dimers) are considered to be macromolecules. When associated with the polyketals of the invention, a macromolecule may be chemically modified prior to being associated with said biodegradable biocompatible polyketal.

"Diagnostic label": As used herein, the term diagnostic label refers to an atom, group of atoms, moiety or functional group, a nanocrystal, or other discrete element of a composition of matter, that can be detected in vivo or ex vivo using analytical methods known in the art. When associated with a biodegradable biocompatible polyketal of the present invention, such diagnostic labels permit the monitoring of the biodegradable biocompatible polyketal in vivo. On the other hand, constructs and compositions that include diagnostic labels can be used to monitor biological functions or structures. Examples of diagnostic labels include, without limitations, labels that can be used in medical diagnostic procedures, such as, radiopharmaceutical or radioactive isotopes for gamma scintigraphy and Positron Emission Tomography (PET), contrast agent for Magnetic Resonance Imaging (MRI) (for example paramagnetic atoms and superparamagnetic nanocrystals), contrast agent for computed tomography, contrast agent for X-ray imaging method, agent for ultrasound diagnostic method, agent for neutron activation, and moiety which can reflect, scatter or affect X-rays, ultrasounds, radiowaves and microwaves, fluorophores in various optical procedures, etc.

"Effective amount of a glycol-specific oxidizing agent": as it relates to the oxidative cleavage of the polysaccharides referred to in the present invention, the phrase effective amount of a glycol-specific oxidizing agent means an amount of the glycol-specific oxidizing agent that provides oxidative opening of essentially all carbohydrate rings of a polysaccharide.

"Aliphatic": In general, the term aliphatic, as used herein, includes both saturated and unsaturated, straight chain (i.e., unbranched) or branched aliphatic hydrocarbons, which are optionally substituted with one or more functional groups, as defined below. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms. In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms.

Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents, as previously defined. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

"Alicyclic": The term alicyclic, as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups, as defined below. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl-n, cyclohexyl, —$CH_2$-cyclohexyl, cyclohexenylethyl, cyclohexanylethyl, norbornyl moieties and the like, which again, may bear one or more substituents.

"Heteroaliphatic": The term "heteroaliphatic", as used herein, refers to aliphatic moieties in which one or more carbon atoms in the main chain have been substituted with an heteroatom. Thus, a heteroaliphatic group refers to an aliphatic chain which contains one or more oxygen sulfur, nitrogen, phosphorus or silicon atoms, e.g., in place of carbon atoms. Heteroaliphatic moieties may be saturated or unsaturated, branched or linear (i.e., unbranched), and substituted or unsubstituted. Substituents include, but are not limited to, any of the substitutents mentioned below, i.e., the substituents recited below resulting in the formation of a stable compound.

"Heteroalicyclic": The term heteroalicyclic, as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups. Substituents include, but are not limited to, any of the substitutents mentioned below, i.e., the substituents recited below resulting in the formation of a stable compound.

"Alkyl": the term alkyl as used herein refers to saturated, straight- or branched-chain hydrocarbon radicals derived from a hydrocarbon moiety containing between one and twenty carbon atoms by removal of a single hydrogen atom, which alkyl groups are optionally substituted with one or more functional groups. Substituents include, but are not limited to, any of the substitutents mentioned below, i.e., the substituents recited below resulting in the formation of a stable compound. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl.

"Alkoxy": the term alkoxy as used herein refers to an alkyl groups, as previously defined, attached to the parent molecular moiety through an oxygen atom. Examples include, but are not limited to, methoxy, ethoxy, propoxy, isopropoxy, n-butoxy, tert-butoxy, neopentoxy, and n-hexoxy.

"Alkenyl": the term alkenyl denotes a monovalent group derived from a hydrocarbon moiety having at least one carbon-carbon double bond by the removal of a single hydrogen atom, which alkenyl groups are optionally substituted with one or more functional groups. Substituents include, but are not limited to, any of the substitutents mentioned below, i.e., the substituents recited below resulting in the formation of a stable compound. Alkenyl groups include, for example, ethenyl, propenyl, butenyl, 1-methyl-2-buten-1-yl, and the like.

"Alkynyl": the term alkynyl as used herein refers to a monovalent group derived form a hydrocarbon having at least one carbon-carbon triple bond by the removal of a single hydrogen atom, which alkenyl groups are optionally substituted. Substituents include, but are not limited to, any of the substitutents mentioned below, i.e., the substituents recited below resulting in the formation of a stable compound. Representative alkynyl groups include ethynyl, 2-propynyl (propargyl), 1-propynyl, and the like.

"Amine": the term amine as used herein refers to one, two, or three, respectively, alkyl groups, as previously defined, attached to the parent molecular moiety through a nitrogen atom. The term alkylamino refers to a group having the structure —NHR' wherein R' is an alkyl group, as previously defined; and the term dialkylamino refers to a group having the structure —NR'R", wherein R' and R" are each independently selected from the group consisting of alkyl groups. The term trialkylamino refers to a group having the structure —NR'R"R''', wherein R', R", and R''' are each independently selected from the group consisting of alkyl groups. Additionally, R', R", and/or R''' taken together may optionally be —(CH$_2$)$_k$— where k is an integer from 2 to 6. Example include, but are not limited to, methylamino, dimethylamino, ethylamino, diethylamino, diethylaminocarbonyl, methylethylamino, iso-propylamino, piperidino, trimethylamino, and propylamino.

"Aryl": The term aryl, as used herein, refers to stable mono- or polycyclic, unsaturated moieties having preferably 3-14 carbon atoms, each of which may be substituted or unsubstituted. Substituents include, but are not limited to, any of the substitutents mentioned below, i.e., the substituents recited below resulting in the formation of a stable compound. The term aryl may refer to a mono- or bicyclic carbocyclic ring system having one or two aromatic rings including, but not limited to, phenyl, naphthyl, tetrahydronaphthyl, indanyl, indenyl and the like.

"Heteroaryl": The term heteroaryl, as used herein, refers to a stable heterocyclic or polyheterocyclic, unsaturated radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms. Heteroaryl moieties may be substituted or unsubstituted. Substituents include, but are not limited to, any of the substitutents mentioned below, i.e., the substituents recited below resulting in the formation of a stable compound. Examples of heteroaryl nuclei include pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an aliphatic, alicyclic, heteroaliphatic, heteroalicyclic, alkyl or heteroalkyl moiety and thus also include -(aliphatic)aryl, -(heteroaliphatic)aryl, -(aliphatic)heteroaryl, -(heteroaliphatic)heteroaryl, -(alkyl) aryl, -(heteroalkyl)aryl, -(heteroalkyl)aryl, and -(heteroalkyl) heteroaryl moieties. Thus, as used herein, the phrases "aryl or heteroaryl" and "aryl, heteroaryl, -(aliphatic)aryl, -(heteroaliphatic)aryl, -(aliphatic)heteroaryl, -(heteroaliphatic) heteroaryl, -(alkyl)aryl, -(heteroalkyl)aryl, -(heteroalkyl) aryl, and -(heteroalkyl)heteroaryl" are interchangeable.

"Carboxylic acid": The term carboxylic acid as used herein refers to a group of formula —CO$_2$H.

"Halo, halide and halogen": The terms halo, halide and halogen as used herein refer to an atom selected from fluorine, chlorine, bromine, and iodine.

"Methylol": The term methylol as used herein refers to an alcohol group of the structure —CH$_2$OH.

"Hydroxyalkyl": As used herein, the term hydroxyalkyl refers to an alkyl group, as defined above, bearing at least one OH group.

"Mercaptoalkyl": The term mercaptoalkyl as used therein refers to an alkyl group, as defined above, bearing at least one SH group "Heterocyclic": The term heterocyclic, as used herein, refers to a non-aromatic partially unsaturated or fully saturated 3- to 10-membered ring system, which includes single rings of 3 to 8 atoms in size and bi- and tri-cyclic ring systems which may include aromatic six-membered aryl or aromatic heterocyclic groups fused to a non-aromatic ring. Heterocyclic moieties may be substituted or unsubstituted. Substituents include, but are not limited to, any of the substitutents mentioned below, i.e., the substituents recited below resulting in the formation of a stable compound. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized.

"Acyl": The term acyl, as used herein, refers to a group comprising a carbonyl group of the formula C=O. Examples of acyl groups include aldehydes, ketones, carboxylic acids, acyl halides, anhydrides, thioesters, amides and carboxylic esters.

"Hydrocarbon": The term hydrocarbon, as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions.

"Substituted": The terms substituted, whether preceded by the term "optionally" or not, and substituent, as used herein, refers to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Examples of substituents include, but are not limited to aliphatic; alicyclic; heteroaliphatic; heteroalicyclic; aryl; heteroaryl; alkylaryl;

alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$^x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted.

The following are more general terms used throughout the present application:

"Animal": The term animal, as used herein, refers to humans as well as non-human animals, at any stage of development, including, for example, mammals, birds, reptiles, amphibians, fish, worms and single cells. Cell cultures and live tissue samples are considered to be pluralities of animals. Preferably, the non-human animal is a mammal (e.g., a rodent, a mouse, a rat, a rabbit, a monkey, a dog, a cat, a primate, or a pig). An animal may be a transgenic animal or a human clone.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, or combinations thereof, etc.

"Effective amount": In general, as it refers to an active agent or drug delivery device, the term "effective amount" refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, etc. For example, the effective amount of microparticles containing an antigen to be delivered to immunize an individual is the amount that results in an immune response sufficient to prevent infection with an organism having the administered antigen.

DETAILED DESCRIPTION OF CERTAIN PREFERRED EMBODIMENTS OF THE INVENTION

Figure 1:
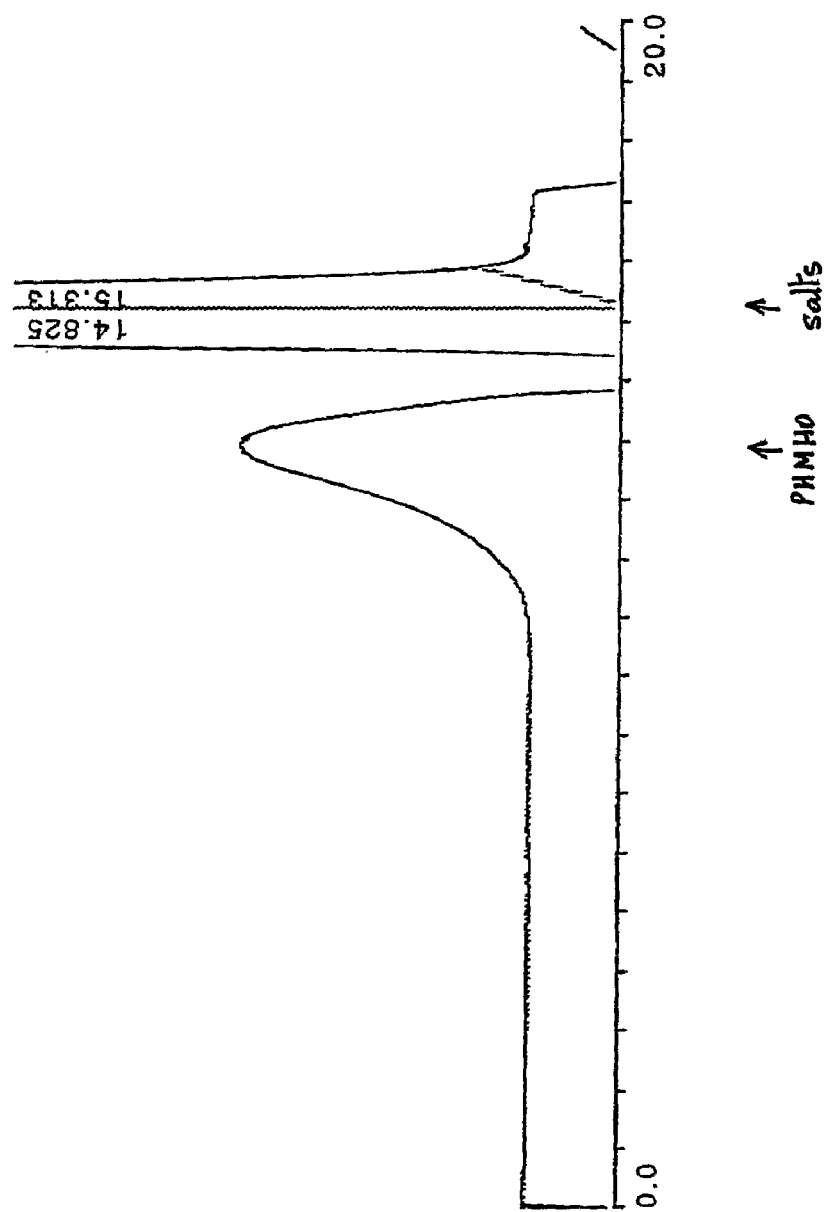
FIG. 1 depicts the size exclusion chromatogram of the reaction mixture obtained in Example 2, containing poly[1-hydroxymethyl-1-(2-hydroxy-1-hydroxymethyl-ethoxy)-ethylene oxide] (e.g., PHMHO), the product of oxidative cleavage/reduction of inulin. Detection: refraction index. Column: BioRad BioSil SEC 125. Eluent: water, 0.9% NaCl. Apparent MW: 3 tp 7 kDa (90% of material).

Certain preferred embodiments of the invention will now be more particularly described and pointed out in the claims. It will be understood that the particular embodiments of the invention are shown by way of illustration and not as limitations of the invention. The principle features of the invention may be employed in various embodiments without departing from the scope of the invention.

Biodegradable Biocompatible Polyketals

Novel concepts in pharmacology and bioengineering impose new, more specific and more stringent requirements on biomedical polymers. Ideally, advanced macromolecular materials would combine negligible reactivity in vivo with low toxicity and biodegradability. Polymer structure should support an ample set of technologies for polymer derivatization, for example, conjugation with drugs, cell-specific ligands, or other desirable modifiers. Materials combining all the above features would be useful in the development of macromolecular drugs, drug delivery systems, implants and templates for tissue engineering.

On the chemistry level, developing such biocompatible and biodegradable materials translates into developing macromolecules with minimized interactions in vivo, main chains susceptible to hydrolysis (e.g., degradation) in vivo, and readily modifiable functional groups. Another consideration to take into account is that both the main chain and the functional groups interact with an extremely complex biological milieu, and all interactions may be amplified via cooperative mechanisms.

Biomolecule interactions in vivo are mediated by several components of cell surfaces, extracellular matrix, and biological fluids. For example, both biomolecule internalization by cells and cell adhesion to polymer-coated surfaces can be mediated by several cell surface elements, many of which are functionally specialized. Cooperative binding, often referred to as "non-specific interactions", is another major factor of biomolecule (and surface) reactivity in vivo. Cell interactions with polymers and recognition protein-polymer complexes also have an element of cooperativity. The very nature of cooperative interactions in complex systems suggests that any large molecule can significantly interact with a complex substrate for the simple reason that, because the binding energy is additive, the association constant of cooperative binding ($K_a$) would grow with the number of associations exponentially. In other words, any polymer of a sufficient length can be expected to interact with at least one of the various components of a biological system. Even if a molecule of certain size shows low interactions in cell cultures and in vivo, a larger molecule of the same type (or a supra molecular assembly) can have a much higher binding activity.

In summary, even if polymer molecules are assembled of domains that do not interact with cell receptors and recognition proteins, such molecules can be capable of cooperative interactions in vivo; i.e., completely inert polymers may not exist at all. However, several biomolecules and biological interfaces do appear to be functionally inert, except for their specialized signaling domains. For example, plasma proteins are known to circulate for several weeks without uptake in the reticuloendothelial system (RES), unlike artificial constructs of comparable size that have never been reported to have comparable blood half-lives. Without wishing to be bound to any particular theory, we propose that the mutual "inertness" of natural biomolecules and surfaces may relate to their relatively uniform interface structures, where the potential binding sites are always saturated by naturally occurring counteragents present in abundance. Therefore, emulation of the common interface structures can result in a material that would not actively interact with actually existing binding sites because these sites would be pre-occupied by the natural "prototypes".

Poly- and oligosaccharides are the most abundant interface molecules expressed (as various glycoconjugates) on cell surfaces, plasma proteins, and proteins of the extracellular matrix. Therefore, the invention encompasses structural emulation of interface carbohydrates in an effort to identify and exclude all structural components that can be recognized, even with low affinity, by any biomolecule, especially by cell receptors and recognition proteins.

All interface carbohydrates have common structural domains which appear to be irrelevant to their biological function. The acetal/ketal group and the adjacent atoms are present in all carbohydrates regardless of biological activity, whereas the receptor specificity of each molecule depends on the structure and configuration of the glycol domains of the carbohydrate rings. Thus it would seem that biologically inert ("stealth") polymers could be obtained using substructures that form the acetal/ketal structures of the carbohydrate rings; i.e., the —O—C—O— group and adjacent carbons. Although functional groups that are common in naturally occurring glycoconjugates (e.g., OH groups) can be used as substitutents, the potentially biorecognizable combinations of these groups, such as rigid structures at C1-C2-C3-C4 (in pyranoses) is not desirable.

The present invention is founded on the recognition that the macromolecular products of the cleavage of at least one of the carbon-carbon bonds in the C1-C2-C3-C4 portion in substantially all the carbohydrate rings of a polysaccharide would have the desired properties (e.g., an essentially inert biocompatible hydrophilic polymer). In addition, synthetic strategies designed to position the polysaccharide acetal/ketal groups within the main chain of the resulting macromolecular product would ensure degradability via proton-catalyzed hydrolysis.

Biocompatible biodegradable polyacetals according to this concept have been described in U.S. Pat. Nos. 5,811,510; 5,863,990 and 5,958,398, incorporated herein by reference (Papisov M., "Biodegradable Polyacetal Polymers and Methods for their Formation and Use"). Polyacetals differ from polyketals in that the structure of their hydrolysis sensitive group is —O—CHR—O— (polyacetals) rather than —O—CR$^1$R$^2$—O— (polyketals). This difference results in the generally different physical shape of the polymer molecule, different depolymerization products, and can provide products with different and useful sensitivity to pH, the action of water and other reagents. In addition, polyketals may offer various other advantages over polyacetals. For example, polyketals generally have more functional groups per monomer unit, which allows a higher degree of derivatization. In addition, without wishing to be bound by any particular theory, we propose that the increased steric hindrance of the ketal group caused by the additional substituent may result in polymers with higher resistance to the components of normal biological milieu. This increased steric hinderance may also translate into longer material lifetime in chiral separation applications. Another advantage of the present invention is that several known polyketoses found in plants, such as levans and other fructans, which currently have no use, can be transformed into useful products. Cells producing such polysaccharides may be selected, cloned and transformed to produce, after polysaccharide treatment, polyketals with novel and more useful structures and properties. Yet another advantage of the polyketals of the present invention resides in the different chemical structure of terminal groups of polyketals, for example polyketals derived from 1,2-ketoses. For instance, upon partial hydrolysis, the resulting fragments of such polyketals comprise a terminal ketone group, which allows selective one-stage terminal modification. In another aspect, the polyketals of the invention present the additional advantage that depolymerization of protected hydrophilic polyketals can provide inexpensive protected derivatives of substituted ketones, which may be valuable in organic synthesis. In addition, another advantage is that different functional group geometry may provide better polycationic polyketals for DNA packaging for non-viral gene therapy.

The present invention encompasses biodegradable biocompatible hydrophilic polyketals, derivatives and conjugates thereof, as well as methods of preparation and methods of use thereof.

As described in Example 1, we have successfully made biodegradable biocompatible polyketals which are hydrophilic, hydrolyzable and can be functionalized to include pharmaceutically useful groups. In a preferred embodiment, the polyketals of the present invention have at least one of the ketal oxygen atoms in each monomer unit positioned within the main chain. This ensures that the degradation process (via hydrolysis/cleavage of the polymer ketal groups) will result in fragmentation of the polyketal to the monomeric components (i.e., degradation), and confers to the polyketals of the invention their biodegradable properties. The properties (e.g., solubility, bioadhesivity and hydrophilicity) of biodegradable biocompatible polyketals can be modified by subsequent substitution of additional hydrophilic or hydrophobic groups. The novelty of the present invention relates in part to the structure and properties of hydrophilic polyketals comprising ketal groups in the main chain.

Synthetic methods for the preparation of polymers containing ketal groups are known in the art (see for example, "Hydrophobically modified poly(acetal-polyethers)" Sau A. C., U.S. Pat. No. 5,574,127; "Method for preparing polyacetals and polyketals by emulsion polymerization" Chou Y. J. et al., U.S. Pat. No. 4,374,953; "Positive-working radiation-sensitive copying composition and method of using to form relief images: Sander J. et al., U.S. Pat. No. 4,247,611). However, a number of them contain ketal groups outside the main chain; e.g., on substitutents or as chemical modifiers for polyketones (see for example "Method for converting polyketals to polyaryletherketones in the presence of a metal salt" Kelsey D. R., U.S. Pat. No. 4,882,397). Thus hydrolysis of the ketal groups in such polymeric materials, unlike the polymers of the present invention, does not result in degradation (depolymerization) of the polymer.

Polyketals known in the art generally comprise hydrophobic substituents and thus generally have limited water solubility. In addition, the methods of making them generate relatively low molecular weight polymers (5-50 kDa). Additionally, most polyketals have hydrophobic domains and, consequently, their biocompatibility is limited. Hydrophobic polymers are vulnerable to non-specific interactions with proteins and lipids, which also may cause undesirable side effects. Finally, most known synthetic polyketals typically have a hydrophobic main chain that does not degrade readily in vivo.

In summary, while a person of ordinary skill in the art has a variety of available synthetic methods at their disposal to prepare polyketals, there is no motivation to select biocompatible, biodegradable, hydrophilic polyketals. Furthermore, even if there was motivation to do so, there is no reasonable expectation that it would succeed. The present invention provides (i) access to biocompatible biodegradable hydrophilic polyketals, (ii) methods for their preparation and (iii) examples of applications where they might find use.

In a preferred embodiment, the polymers of the present invention comprise ketal groups within the main chain. Although it is not necessary that the entire ketal group be positioned within the polymer backbone, it is desirable that at least one of the ketal oxygen atoms belongs to the main chain. Accordingly, one embodiment of the present invention provides biodegradable biocompatible polyketals comprising repeat structural units, wherein substantially all the structural units comprise (i) at least one ketal group wherein at least one ketal oxygen atom is within the polymer main chain; and (ii) at least one hydrophilic group or pharmaceutically useful group. In another aspect of the invention, at least a subset of the repeat structural units have the following chemical structure:

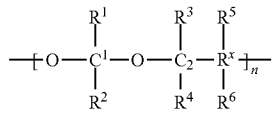

wherein each occurrence of $R^1$ and $R^2$ is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ is either hydrophilic or pharmaceutically useful.

In yet another aspect, the biodegradable biocompatible polyketals of the invention comprise repeat structural units having the following chemical structure:

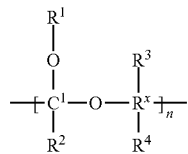

wherein each occurrence of $R^2$ is a biocompatible group and includes a carbon atom covalently attached to $C^1$; $R^x$ includes a carbon atom covalently attached to $C^1$; n is an integer; each occurrence of $R^1$, $R^3$ and $R^4$ is a biocompatible group and is independently hydrogen or an organic moiety; and for each occurrence of the bracketed structure n, at least one of $R^1$, $R^2$, $R^3$ and $R^4$ is either hydrophilic or pharmaceutically useful.

Examples of suitable organic moieties are aliphatic groups having a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters, polythioesters, pharmaceutically useful groups, a biologically active substance or a diagnostic label.

In preferred embodiments of the present invention, for each occurrence of the bracketed structure n, at least one of $R^1$, $R^2$, $R^3$, $R^4$, $R^5$ and $R^6$ includes a carboxyl group (COOH), an aldehyde group (CHO), a methylol ($CH_2OH$) or a glycol group. In another preferred embodiment of the present invention, at least one of $R^1$, $R^2$, $R^3$, $R^4$, $R^5$ and $R^6$ contains an atom or a moiety that increases the polymer hydrophilicity or allows conjugation with other compounds.

In still another preferred embodiment of the present invention $R^1$, $R^2$, $R^3$, $R^4$, $R^5$ or $R^6$ are methylol or glycol. In yet another preferred embodiment of the present invention, $R^1$ and $R^2$ comprise a methylol or glycol group and $R^3$, $R^4$, $R^5$ and $R^6$ are hydrogen.

In exemplary embodiments of the invention, the polyketal comprises the following chemical structure:

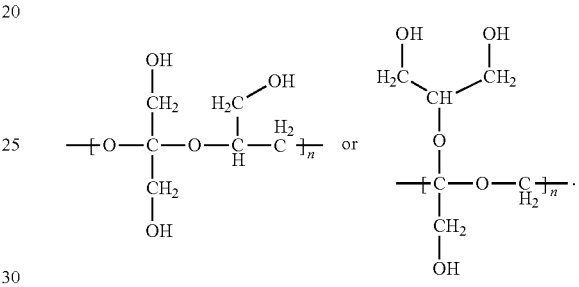

In yet another embodiment of the present invention, at least one of $R^1$, $R^2$, $R^3$, $R^4$, $R^5$ and $R^6$ contains a chiral moiety. In exemplary embodiments of the invention, the polyketal comprises the following chemical structure:

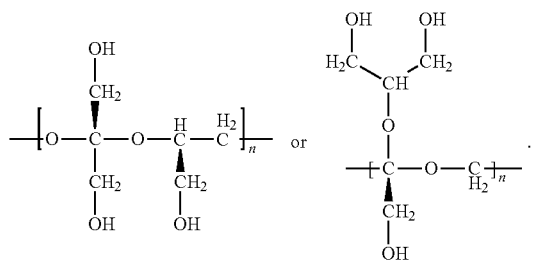

In yet another embodiment of the present invention, at least one of $R^1$, $R^2$, $R^3$, $R^4$, $R^5$ and $R^6$ is a nitrogen-containing compound. The nitrogen-containing compound can be a pharmaceutically useful group, a drug, a macromolecule, a diagnostic label, a crosslinking agent or a functional group which is suitable as a modifier of biodegradable biocompatible polyketal behavior in vivo. Examples of such functional groups include antibodies, their fragments, receptor ligands and other compounds that selectively interact with biological systems.

Alternatively, the nitrogen-containing compound can have a chemical structure of $—C_mH_{2m}NR^7R^8$, wherein m is an integer. In one embodiment, n is one. $R^7$ and $R^8$ can include hydrogen, organic or inorganic substituents. Examples of suitable organic or inorganic groups include aliphatic groups, aromatic groups, complexes of heavy metals, etc.

In one aspect of the invention, the biodegradable biocompatible polyketals can be crosslinked. A suitable crosslinking agent has the formula $X^1—(R)—X^2$, where R is a spacer group and $X^1$ and $X^2$ are reactive groups. $X^1$ and $X^2$ can be different or the same. The spacer group R may be an aliphatic, alicyclic, heteroaliphatic, heteroalicyclic, aryl or heteroaryl moiety. Examples of suitable spacer groups include biodegradable or nonbiodegradable groups, for example, aliphatic groups, carbon chains containing biodegradable inserts such as disulfides, esters, etc. The term "reactive group," as it relates to $X^1$ and $X^2$, means functional groups which can be connected by a reaction within the biodegradable biocompatible polyketals, thereby crosslinking the biodegradable biocompatible polyketals. Suitable reactive groups which form crosslinked networks with the biodegradable biocompatible polyketals include epoxides, halides, tosylates, mesylates, carboxylates, aziridines, cyclopropanes, esters, N-oxysuccinimide esters, disulfides, anhydrides etc.

In one of the preferred embodiments of the present invention, the biodegradable biocompatible polyketals are crosslinked with epibromohydrin, or epichlorohydrin. More preferably, the epibromohydrin or epichlorohydrin is present in an amount in the range of between about one and about twenty five percent by weight of the crosslinked biodegradable biocompatible polyketals.

Alternatively, the term "reactive" group as it relates to $X^1$ and $X^2$ means a nucleophilic group that can be reacted with an aldehyde intermediate of the biodegradable biocompatible polyketals, thereby crosslinking the biodegradable biocompatible polyketals. Suitable reactive groups for the aldehyde intermediate include amines, thiols, polyols, alcohols, ketones, aldehydes, diazocompounds, boron derivatives, ylides, isonitriles, hydrazines and their derivatives and hydroxylamines and their derivatives, etc.

In one embodiment, the biodegradable biocompatible polyketals of the present invention have a molecular weight of between about 0.5 and about 1500 kDa. In a preferred embodiment of the present invention, the biodegradable biocompatible polyketals have a molecular weight of between about 1 and about 1000 kDa.

In one embodiment, polyketals are modified at one or both of the termini, for example:

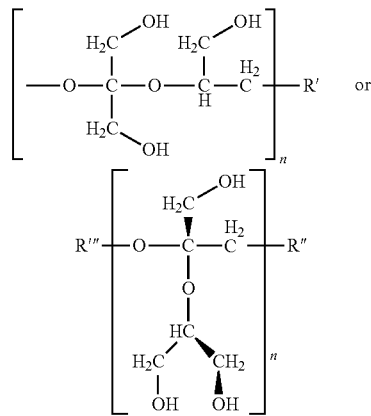

wherein n is an integer and R', R" and R'" may be hydrophilic, pharmaceutically useful, or otherwise useful for the purposes of this invention. For example, R' can comprise an N-hydroxysuccinimide ester or a maleimide for conjugation with proteins; R" and R'" can comprise a phospholipid and a target specific moiety, such as antibody, respectively, for liposome modification.

In another embodiment, polyketals can be substituted at one terminal and one or more non-terminal positions, or at both terminal and one or more non-terminal positions.

In one embodiment, at least one of $R^1$, $R^2$, $R^3$, $R^4$, $R^5$ and $R^6$ can comprise a small molecule, a pharmaceutically useful group, a drug, a macromolecule or a diagnostic label. Examples of suitable drug molecules comprise a biologically active functional group fragment or moiety. Specific examples of suitable drug molecules include vitamins, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or antithrombotic agents, local anesthetics, ophthalmics, prostaglandins, anti-depressants, anti-psychotic substances, anti-emetics, and imaging agents.

Examples of pharmaceutically useful groups include, but are not limited to: hydrophilicity/hydrophobicity modifiers, pharmacokinetic modifiers, antigens, receptor ligands, nucleotides, chemotherapeutic agents, antibacterial agents, antiviral agents, immunomodulators, hormones and their analogs, enzymes, inhibitors, alkaloids, therapeutic radionuclides, etc. Suitable chemotherapeutic compounds are, for example, topoisomerase I and II inhibitors, alkylating agents, anthracyclines, doxorubicin, cisplatin, carboplatin, vincristine, mitromycine, taxol, camptothecin, antisense oligonucleotides, ribozymes, dactinomycines, etc. Other suitable compounds include therapeutic radionuclides, such as β-emitting isotopes of rhenium, cesium, iodine, and alkaloids, etc. In one embodiment of the present invention, at least one of $R^1$, $R^2$, $R^3$, $R^4$, $R^5$ and $R^6$ contains doxorubicin, taxol, or camptothecin.

In another embodiment of the present invention, at least one of $R^1$, $R^2$, $R^3$, $R^4$, $R^5$ and $R^6$ comprises a diagnostic label. Examples of suitable diagnostic labels include diagnostic radiopharmaceutical or radioactive isotopes for gamma scintigraphy and PET, contrast agent for Magnetic Resonance Imaging (MRI) (for example paramagnetic atoms and superparamagnetic nanocrystals), contrast agent for computed tomography, contrast agent for X-ray imaging method, agent for ultrasound diagnostic method, agent for neutron activation, and moiety which can reflect, scatter or affect X-rays, ultrasounds, radiowaves and microwaves, fluorophores in various optical procedures, etc. Diagnostic radiopharmaceuticals include γ-emitting radionuclides, e.g., indium-111, technetium-99m and iodine-131, etc. Contrast agents for MRI (Magnetic Resonance Imaging) include magnetic compounds, e.g. paramagnetic ions, iron, manganese, gadolinium, lanthanides, organic paramagnetic moieties and superparamagnetic, ferromagnetic and antiferromagnetic compounds, e.g., iron oxide colloids, ferrite colloids, etc. Contrast agents for computed tomography and other X-ray based imaging methods include compounds absorbing X-rays, e.g., iodine, barium, etc. Contrast agents for ultrasound based methods include compounds which can absorb, reflect and scatter ultrasound waves, e.g., emulsions, crystals, gas bubbles, etc. Still other examples include substances useful for neutron activation, such as boron and gadolinium.

Further, substituents can be employed which can reflect, refract, scatter, or otherwise affect X-rays, ultrasound, radiowaves, microwaves and other rays useful in diagnostic procedures. Fluorescent labels can be used for photoimaging. In a preferred embodiment, at least one of $R^1$, $R^2$ and $R^3$ comprises a paramagnetic ion or group.

In yet another embodiment, the polyketals of the present invention are associated with a macromolecule. Examples of suitable macromolecules include, but are not limited to, enzymes, polypeptides, polylysine, proteins, lipids, polyelectrolytes, antibodies, ribonucleic and deoxyribonucleic acids and lectins. The macromolecule may be chemically modified prior to being associated with said biodegradable biocompatible polyketal. Circular and linear DNA and RNA (e.g., plasmids) and supramolecular associates thereof, such as viral particles, for the purpose of this invention are considered to be macromolecules.

Polyketals according to the present invention are expected to be biodegradable, in particular upon uptake by cells, and relatively "inert" in relation to biological systems. The products of degradation are preferably uncharged and do not significantly shift the pH of the environment.

In one embodiment, postsynthetic modification of the polyketals of the invention allows the introduction of a variety of functional groups. It is proposed that the abundance of alcohol groups may provide low rate of polymer recognition by cell receptors, particularly of phagocytes. The polymer backbones of the present invention generally contain few, if any, antigenic determinants (characteristic, for example, for polysaccharides and polypeptides) and generally do not comprise rigid structures capable of engaging in "key-and-lock" type interactions. Thus, the soluble, crosslinked and solid polyketals of this invention are predicted to have low toxicity and bioadhesivity, which makes them suitable for several biomedical applications.

Biodegradable Biocompatible Polyketals—Methods of Preparation

According to the present invention, any available techniques can be used to make the inventive polyketals or compositions including them. For example, semi-synthetic and fully synthetic methods such as those discussed in detail below may be used.

Certain compounds of the present invention, and definitions of specific functional groups are also described in more detail herein. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, certain exemplary oxygen protecting groups may be utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

Semi-Synthetic Route

In a preferred embodiment, the carbohydrate rings of a suitable polysaccharide can be oxidized by glycol-specific reagents, resulting in the cleavage of carbon-carbon bonds between carbon atoms that are each connected to a hydroxyl group. For example, without wishing to be bound to any particular theory, we propose that oxidative cleavage of 1->2 polyfructoses (a.k.a. 2,1-polyfructoses) in accordance with the present invention proceeds through the following mechanism:

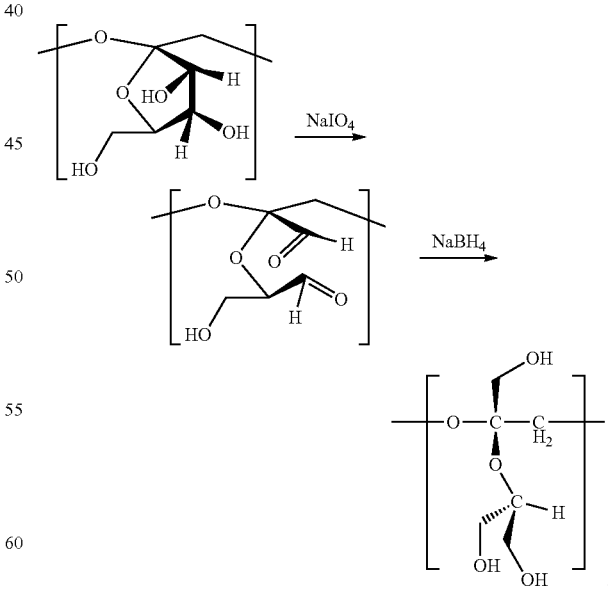

This process can be complicated, depending on experimental conditions, by the formation of intra and interpolymer hemiacetals which can inhibit further polysaccharide oxidation. Oxidative cleavage of polysaccharides applied to the preparation of hydrophilic polyacetals has been reported (U.S. Pat. Nos. 5,811,510; 5,863,990; 5,958,398). The preparation of hydrophilic polyketals by this method, however, has remained unsuccessful until recently. Previous attempts failed to produce the expected polyketal chain, and yielded a fragmented product instead, whereby the polymeric backbone was cleaved during the reaction. The identification of suitable polysaccharides as starting material, together with the optimization of the reaction conditions to achieve better control of the oxidative opening ("lateral cleavage") of the polysaccharide rings, resulted in the successful preparation of hydrophilic polyketals in high yield and high molecular weights. Thus, in the present invention, it can be demonstrated that the oxidation of a suitable polysaccharide, followed by reduction, leads to the synthesis of macromolecular biodegradable biocompatible polyketals. The structure of the biodegradable biocompatible polyketal obtained by the above mentioned method is dependent upon the precursor polysaccharide.

In one embodiment, a method for forming the biodegradable biocompatible polyketals of the present invention comprises a process by which a suitable polysaccharide is combined with an effective amount of a glycol-specific oxidizing agent to form an aldehyde intermediate. The aldehyde intermediate, which is a polyketal of this invention by itself, is then reacted with a suitable reagent to form a biodegradable biocompatible polyketal comprising repeat structural units, wherein substantially all the structural units comprise (i) at least one ketal group wherein at least one ketal oxygen atom is within the polymer main chain; and (ii) at least one hydrophilic group or pharmaceutically useful group. Thus, in certain embodiments, a method for forming the biodegradable biocompatible polyketals comprises steps of: a) reacting an effective amount of an oxidizing agent with a polysaccharide to form a biodegradable biocompatible polyketal aldehyde; b) optionally treating the biodegradable biocompatible polyketal aldehyde with a suitable reagent under suitable conditions to form said biodegradable biocompatible polyketal polymer; and c) optionally repeating step b) until the desired functionalization of said biodegradable biocompatible polyketal is achieved; thereby forming a biodegradable biocompatible polyketal comprising repeat structural units, wherein substantially all the structural units comprise: i) at least one ketal group wherein at least one ketal oxygen atom is within the polymer main chain; and ii) at least one hydrophilic group or pharmaceutically useful group.

In another embodiment, at least a subset of the repeat structural units have the following chemical structure:

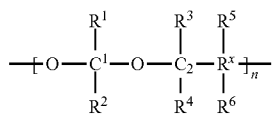

wherein each occurrence of $R^1$ and $R^2$ is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ is either hydrophilic or pharmaceutically useful.

In yet another embodiment, the biodegradable biocompatible polyketals of the invention comprise repeat structural units having the following chemical structure:

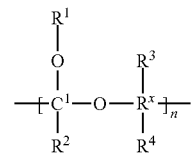

wherein each occurrence of $R^2$ is a biocompatible group and includes a carbon atom covalently attached to $C^1$; $R^x$ includes a carbon atom covalently attached to $C^1$; n is an integer; each occurrence of $R^1$, $R^3$ and $R^4$ is a biocompatible group and is independently hydrogen or an organic moiety; and for each occurrence of the bracketed structure n, at least one of $R^1$, $R^2$, $R^3$ and $R^4$ is either hydrophilic or pharmaceutically useful.

Examples of suitable organic moieties include, but are not limited to, aliphatic groups having a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters, polythioesters, pharmaceutically useful groups, a biologically active substance or a diagnostic label.

The biodegradable biocompatible polyketals of the invention can be prepared to meet desired requirements of biodegradability and hydrophilicity. For example, under physiological conditions, a balance between biodegradability and stability can be reached. For instance, it is known that macromolecules with molecular weights beyond a certain threshold (generally, above 50-100 kDa, depending on the physical shape of the molecule) are not excreted through kidneys, as small molecules are, and can be cleared from the body only through uptake by cells and degradation in intracellular compartments, most notably lysosomes. This observation exemplifies how functionally stable yet biodegradable materials may be designed by modulating their stability under general physiological conditions (pH=7.5±0.5) and at lysosomal pH (pH near 5). For example, hydrolysis of ketal groups is known to be catalyzed by acids, therefore polyketals will be in general less stable in acidic lysosomal environment than, for example, in blood plasma. One can design a test to compare polymer degradation profile at, for example, pH=5 and pH=7.5 at 37° C. in aqueous media, and thus to determine the expected balance of polymer stability in normal physiological environment and in the "digestive" lysosomal compartment after uptake by cells. Polymer integrity in such tests can be measured, for example, by size exclusion HPLC. In many cases, it will be preferable that at pH=7.5 the effective size of the polymer will not detectably change over 1 to 7 days, and remain within 50% from the original for at least several weeks. At pH=5, on the other hand, the polymer should preferably detectably degrade over 1 to 5 days, and be completely transformed into low molecular weight fragments within a two-week to several-month time frame. Although faster degradation may be in some cases preferable, in general it may be more desirable that the polymer degrades in cells with the rate that does not exceed the rate of metabolization or excretion of polymer fragments by the cells.

In certain embodiments of the present invention, the biodegradable biocompatible polyketals can form linear or branched structures. The biodegradable biocompatible polyketal of the present invention can be chiral (optically active). Optionally, the biodegradable biocompatible polyketal of the present invention can be racemic.

Structure, yield and molecular weight of the resultant polyaldehyde depend on the initial polysaccharide. Polysaccharides that do not undergo significant depolymerization in the presence of glycol-specific oxidizing agents, for example, poly (2,1) and (2,6) fructoses, are preferable. Examples of suitable polysaccharides include alpha and beta 2,1 and 2,6 fructans. Particularly preferred polysaccharides are Inulin, Levans from plants, and bacterial fructans. Examples of suitable glycol-specific oxidizing agents include sodium periodate, lead tetra-acetate, periodic acid, etc. In certain embodiments, the oxidation system consists of a non-specific oxidizing agent in combination with glycol-specific catalyst or and intermediate oxidizer, or an electrochemical cell. Examples of suitable reducing agents include sodium borohydride, sodium cyanoborohydride, etc. Temperature, pH and reaction duration can affect the reaction rate and polymer hydrolysis rate. The reaction is preferably conducted in the absence of light. One skilled in the art can optimize the reaction conditions to obtain polymers of desired composition. The resultant polymeric aldehyde intermediate may be reduced to the corresponding alcohol via a suitable reducing agent. Alternatively, aldehyde groups can be conjugated with a variety of compounds or converted to other types of functional groups. In certain preferred embodiments, under physiological conditions, at least one of the aldehyde groups in the aldehyde-substituted polyketal can exist in a hydrated (hemdiol) form. As such, the aldehyde group is considered a hydrophilic group. In another embodiment, the precursor carbohydrate has a chiral atom outside of the cleavage site. Thus the chirality of that atom is retained, and the polyketal is chiral or optically active.

In certain embodiments, the polyketals of the present invention can contain intermittent irregularities throughout the polyketal, such as incompletely oxidized additional groups or moieties in the main chain or in the side chains, as shown below:

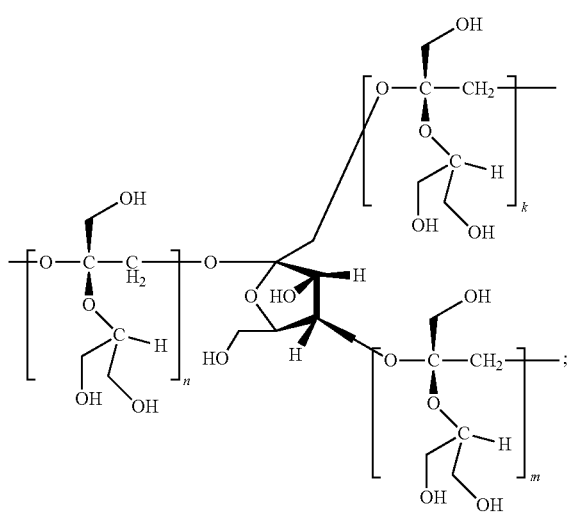

wherein k, m, and n are integers greater than or equal to one.

Although it is generally understood that each ketal unit in a polyketal of the present invention can have different $R^1$, $R^2$, $R^3$, $R^4$, $R^5$ and $R^6$ groups, in a preferred embodiment, more than 50% of the ketal units have the same $R^1$, $R^2$, $R^3$, $R^4$, $R^5$, and $R^6$. For example, preferred polyacetals of this invention include polymers of the general formula:

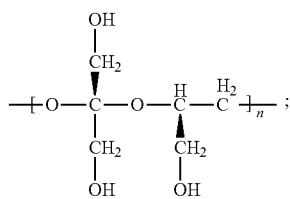

in which 1 to 50% of hydroxyls may further be conjugated with moieties which are either hydrophilic, or pharmaceutically useful. These moieties can be the same (for example, a polyketal conjugated with a drug, such as taxol) or different (for example, a polyketal conjugated with more than one drug, such as taxol and camptothecin, and a targeting moiety, such as a an antibody or a fragment thereof, or a receptor ligand, such as peptide, an oligosaccharide, etc.).

Since it is believed that oxidation does not affect configurations at $C^1$ and $C^2$, the aldehyde intermediate and the polyketal retain the configuration of the parent polysaccharide, and the polyketals can thus be formed in stereoregular isotactic forms.

Fully Synthetic Route

In another preferred embodiment, the biodegradable biocompatible polyketals of the present invention can be prepared by reacting a suitable initiator with a precursor compound comprising the chemical structure:

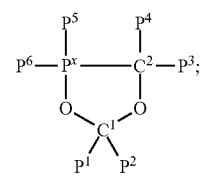

which forms a polymer intermediate comprising the chemical structure:

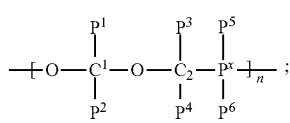

wherein each occurrence of $P^1$ and $P^2$ includes a carbon atom covalently attached to $C^1$ and is independently an organic moiety or a protected organic moiety; $P^x$ includes a carbon atom covalently attached to $C^2$; n is an integer; each occurrence of $P^3$, $P^4$, $P^5$ and $P^6$ is independently hydrogen, an organic moiety or a protected organic moiety. For each occurrence of the bracketed structure n, at least one of $P^1$, $P^2$, $P^3$, $P^4$, $P^5$ and $P^6$ is either a protected hydrophilic group, or a pharmaceutically useful group. In a preferred embodiment, $P^1$, $P^2$, $P^3$, $P^4$, $P^5$ and $P^6$ do not prevent polymerization. Furthermore, $P^1$, $P^2$, $P^3$, $P^4$, $P^5$ and $P^6$ are suitable for conversion to hydrophilic groups as described above. In one embodiment, when appropriate, the protected hydrophilic groups or protected organic moieties of the polymer intermediate are deprotected and optionally derivatized, thereby forming the polyketal comprising the structure:

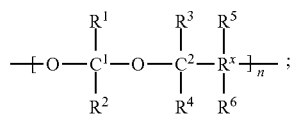

wherein $R^1$ and $R^2$ are biocompatible groups and include a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and at least one of $R^1$, $R^2$, $R^3$, $R^4$, $R^5$ and $R^6$ is either hydrophilic or pharmaceutically useful. Alternatively, other ring opening techniques can be employed or developed, for example employing appropriate catalysts and resulting in the formation of polyketals comprising unsaturated linkages within the main chain. The latter can be further transformed into single bonds using appropriate reagents. Thus, in certain embodiments, a method for forming a biodegradable biocompatible polyketal, comprises steps of: a) reacting a suitable initiator with a compound having the chemical structure:

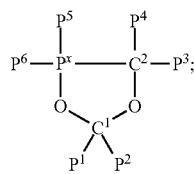

thereby forming a polymer intermediate comprising the chemical structure:

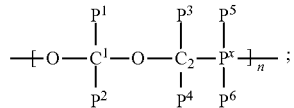

wherein each occurrence of $P^1$ and $P^2$ is independently an organic moiety or a protected organic moiety and includes a carbon atom covalently attached to $C^1$; each occurrence of $P^x$ is an organic moiety and includes a carbon atom covalently attached to $C^2$; n is an integer; each occurrence of $P^3$, $P^4$, $P^5$ and $P^6$ is independently hydrogen, an organic moiety or a protected organic moiety; and for each occurrence of the bracketed structure n, at least one of $P^1$, $P^2$, $P^3$, $P^4$, $P^5$ and $P^6$ is a protected hydrophilic group or a pharmaceutically useful group; b) optionally reacting said polymer intermediate with a suitable reagent under suitable conditions to form second polymer intermediate; and c) optionally repeating step b) until the desired functionalization of said polymer intermediate is achieved; thereby forming a polyketal comprising the structure:

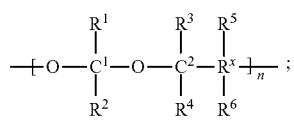

wherein each occurrence of $R^1$ and $R^2$ is independently a biocompatible group and includes a carbon atom covalently attached to $C^1$; each occurrence of $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ is a hydrophilic group or a pharmaceutically useful group.

"Protected hydrophilic group" and "Protected organic moiety" as these terms are used herein, mean a chemical group which will not interfere with decyclization of the precursor compound by the initiator or prevent subsequent polymerization, and which, upon additional treatment by a suitable agent, can be converted to a hydrophilic functional group or an organic moiety, respectively. Examples of protected hydrophilic groups include carboxylic esters, alkoxy groups, thioesters, thioethers, vinyl groups, haloalkyl groups, Fmoc-alcohols, etc.

Examples of suitable organic moieties include, but are not limited to, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters, polythioesters, pharmaceutically useful groups, a biologically active substance or a diagnostic label.

In certain preferred embodiments, the biodegradable biocompatible polyketals of the present invention can be chemically modified by, for example, crosslinking the polyketals to form a gel. The crosslink density of the biodegradable biocompatible polyketal is generally determined by the number of reactive groups in the polyketal and by the number of crosslinking molecules, and can be controlled by varying the ratio of polyketal to the amount of crosslinker present. Thus, in certain embodiments, the invention provides a method for forming a crosslinked biodegradable biocompatible polyketal, comprising steps of: a) reacting an effective amount of an oxidizing agent with a polysaccharide to form an aldehyde intermediate; b) optionally treating the biodegradable biocompatible polyketal aldehyde formed in step (a) with a suitable reagent under suitable conditions to form a polyketal polymer intermediate; c) optionally repeating step b) until the desired functionalization of said polyketal polymer intermediate is achieved; and d) reacting said polyketal polymer intermediate with a crosslinking agent.

In one embodiment, a suitable crosslinking agent has the formula $X^1$—(R)—$X^2$, where R is a spacer group and $X^1$ and $X^2$ are reactive groups. The spacer group R may be an aliphatic, alicyclic, heteroaliphatic, heteroalicyclic, aryl or heteroaryl moiety. Examples of suitable spacer groups include biodegradable or nonbiodegradable groups, for example, aliphatic groups, carbon chains containing biodegradable inserts such as disulfides, esters, etc. The term "reactive group," as it relates to $X^1$ and $X^2$, means functional groups which can be connected by a reaction within the biodegradable biocompatible polyketals, thereby crosslinking the biodegradable biocompatible polyketals. Suitable reactive groups which form crosslinked networks with the biodegradable biocompatible polyketals include epoxides, halides, tosylates, mesylates, carboxylates, aziridines, cyclopropanes, esters, N-oxysuccinimide esters, disulfides, anhydrides etc.

In one of the preferred embodiments of the present invention, the biodegradable biocompatible polyketals are crosslinked with epibromohydrin or epichlorohydrin. More preferably, the epibromohydrin or epichlorohydrin is present in an amount in the range of between about one and twenty five percent by weight of the crosslinked biodegradable biocompatible polyketals.

Alternatively, the term "reactive" group as it relates to $X^1$ and $X^2$ means a nucleophilic group that can be reacted with an aldehyde intermediate of the biodegradable biocompatible polyketals, thereby crosslinking the biodegradable biocompatible polyketals. In certain embodiments, the invention provides a method for forming a crosslinked biodegradable biocompatible polyketal, comprising steps of: a) reacting an effective amount of an oxidizing agent with a polysaccharide to form an aldehyde intermediate; b) optionally treating the biodegradable biocompatible polyketal aldehyde formed in step (a) with a suitable reagent under suitable conditions to form a polyketal polymer intermediate; c) optionally repeating step b) until the desired functionalization of said polyketal polymer intermediate is achieved; and d) reacting said polyketal polymer intermediate with a crosslinking agent.

In certain other embodiments, a method for forming a crosslinked biodegradable biocompatible polyketal comprises steps of: a) reacting an effective amount of an oxidizing agent with a polysaccharide to form an aldehyde intermediate; and b) reacting said aldehyde intermediate with a crosslinking agent.

In certain other embodiments, a method for forming a crosslinked biodegradable biocompatible polyketal comprises steps of: a) reacting a suitable initiator with a compound having the chemical structure:

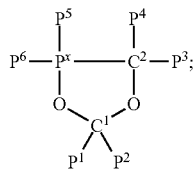

thereby forming a polymer intermediate comprising the chemical structure:

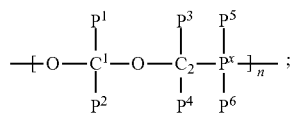

wherein each occurrence of $P^1$ and $P^2$ is independently an organic moiety or a protected organic moiety and includes a carbon atom covalently attached to $C^1$; each occurrence of $P^x$ is an organic moiety which includes a carbon atom covalently attached to $C^2$; n is an integer; each occurrence of $P^3$, $P^4$, $P^5$ and $P^6$ is independently hydrogen, an organic moiety or a protected organic moiety; and for each occurrence of the bracketed structure n, at least one of $P^1$, $P^2$, $P^3$, $P^4$, $P^5$ and $P^6$ is a protected hydrophilic group or a pharmaceutically useful group; b) optionally reacting said polymer intermediate with a suitable reagent under suitable conditions to form second polymer intermediate; c) optionally repeating step b) until the desired functionalization of said polymer intermediate is achieved; and d) reacting the biodegradable biocompatible polyketal formed in step c) with a crosslinking agent.

Suitable reactive groups for the aldehyde intermediate include amines, thiols, polyols, alcohols, ketones, aldehydes, diazocompounds, boron derivatives, ylides, isonitriles, hydrazines and their derivatives and hydroxylamines and their derivatives, etc.

In certain embodiments, the biodegradable biocompatible polyketal can be combined with a suitable aqueous base, such as sodium hydroxide, and crosslinked with epibromohydrin. Control of the amounts of epibromohydrin can determine the degree of crosslinking within the biodegradable biocompatible polyketal gel. For example, biodegradable biocompatible polyketals can be exposed to varying amounts of epibromohydrin for a period of about eight hours at a temperature about 80° C. to form crosslinked biodegradable biocompatible polyketal gels which vary in crosslink density in relation to the amount of epibromohydrin utilized. The crosslinked biodegradable biocompatible polyketal gel can further be reacted with a drug.

Treatment of the biodegradable biocompatible polyketal with a suitable base, such as triethylamine in dimethylsulfoxide (DMSO), and an anhydride provides, for example, a derivatized polyketal solution. Control of the amount of anhydride within the biodegradable biocompatible polyketal can determine the degree of derivitization of the polyketal in the solution.

In another embodiment of the present invention, treatment of polylysine labeled with DPTA (diethylenetriaminepentaacetic acid) with the biodegradable biocompatible polyketal aldehyde, in water, for example, followed by subsequent reduction in water, provides a derivatized polyketal solution.

Polyketals of this invention can have a variety of functional groups that can be readily derivatized. For example, aldehyde groups of an intermediate product of polysaccharide oxidation can be converted not only into alcohol groups, but also into amines, thioacetals, carboxylic acids, amides, esters, thioesters, etc.

In certain embodiments, terminal groups of the polymers of this invention can differ from $R^1$, $R^2$, $R^3$, $R^4$, $R^5$ or $R^6$. Terminal groups can be created, for example, by selective modification of each reducing and non-reducing terminal unit of the precursor polysaccharide. One skilled in the art can utilize known chemical reactions to obtain desired products with varying terminal groups. For example, a hemiketal group at the reducing end of a polyketose can be readily and selectively transformed into a carboxylic acid group (e.g., via formation of a carboxyl-substituted glycoside) and further into a variety of other functional groups.

In one embodiment, the terminal group is such that it allows binding of the polymeric chain to a solid support either directly or via a suitable linker. This has the advantage of allowing solid phase chemical modification of the immobilized polymer to the desired polyketal of the invention. Benefits of this technique include ease of purification by filtration, use of excess reagent for driving reactions to completion, and ease of automation. Examples of suitable solid support are polystyrene, polyethylene glycol, cellulose, controlled pore-glass, etc. . . . Examples of suitable linkers are those that can be cleaved under neutral or basic conditions, such as ester or sulfide linkages.

In one embodiment, the polyketal of the present invention is associated with at least one small molecule, a pharmaceutically useful group, a drug, a macromolecule or a diagnostic label. Examples of suitable drug molecules comprise a biologically active functional group fragment or moiety. Specific examples of suitable drug molecules include vitamins, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or antithrombotic agents, local anesthetics, ophthalmics, prostaglandins, anti-depressants, anti-psychotic substances, anti-emetics, and imaging agents.

Examples of pharmaceutically useful groups include, but are not limited to hydrophilicity/hydrophobicity modifiers, pharmacokinetic modifiers, antigens, receptor ligands, nucleotides, chemotherapeutic agents, antibacterial agents, antiviral agents, immunomodulators, hormones and their analogs, enzymes, inhibitors, alkaloids, therapeutic radionuclides, etc. Suitable chemotherapeutic compounds are, for example, topoisomerase I and II inhibitors, alkylating agents, anthracyclines, doxorubicin, cisplatin, carboplatin, vincristine, mitromycine, taxol, camptothecin, antisense oligonucleotides, ribozymes, dactinomycines, etc. Other suitable compounds include therapeutic radionuclides, such as β-emitting isotopes of rhenium, cesium, iodine, and alkaloids, etc. In one embodiment of the present invention, at least one of $R^1$, $R^2$, $R^3$, $R^4$, $R^5$ and $R^6$ contains doxorubicin.

In another embodiment of the present invention, in at least one ketal unit at least one of $R^1$, $R^2$, $R^3$, $R^4$, $R^5$ and $R^6$ comprises a diagnostic label. Examples of suitable diagnostic labels include diagnostic radiopharmaceutical or radioactive isotopes for gamma scintigraphy and PET, contrast agent for Magnetic Resonance Imaging (MRI) (for example paramagnetic atoms and superparamagnetic nanocrystals), contrast agent for computed tomography, contrast agent for X-ray imaging method, agent for ultrasound diagnostic method, agent for neutron activation, and moiety which can reflect, scatter or affect X-rays, ultrasounds, radiowaves and microwaves, fluorophores in various optical procedures, etc. Diagnostic radiopharmaceuticals include γ-emitting radionuclides, e.g., indium-111, technetium-99m and iodine-131, etc. Contrast agents for MRI (Magnetic Resonance Imaging) include magnetic compounds, e.g. paramagnetic ions, iron, manganese, gadolinium, lanthanides, organic paramagnetic moieties and superparamagnetic compounds, e.g., iron oxide colloids, ferrite colloids, etc. Contrast agents for computed tomography and other X-ray based imaging methods include compounds absorbing X-rays, e.g., iodine, barium, etc. Contrast agents for ultrasound based methods include compounds which can absorb, reflect and scatter ultrasound waves, e.g., emulsions, crystals, gas bubbles, etc. Still other examples include substances useful for neutron activation, such as boron. Further, substituents can be employed which can reflect, scatter, or otherwise affect X-rays, ultrasound, radiowaves, microwaves and other rays useful in diagnostic procedures. In a preferred embodiment, at least one of $R^1$, $R^2$ and $R^3$ comprises a paramagnetic ion or group.

In yet another embodiment, the polyketals of the present invention are associated with a macromolecule. Examples of suitable macromolecules include, but are not limited to, proteins, enzymes, growth factors, cytokines, peptides, polypeptides, polylysine, proteins, lipids, DNA, RNA, polyelectrolytes, antibodies, and lectins. The macromolecule may be chemically modified prior to being associated with said biodegradable biocompatible polyketal.

Biodegradable Polyketal Compositions

In certain embodiments, there is provided a composition comprising the macromolecular product of the lateral cleavage of a polysaccharide; whereby at least one carbon-carbon bond is cleaved in substantially all the carbohydrate moieties of said polysaccharide. In certain exemplary embodiments, the lateral cleavage is effected using an oxidizing agent. In certain other exemplary embodiments, the oxidizing agent is a glycol-specific agent. In still other embodiments, the glycol-specific agent is sodium periodate.

In yet other embodiments, the invention provides a composition comprising the macromolecular product of the lateral cleavage of a polysaccharide; whereby at least one carbon-carbon bond is cleaved in substantially all the carbohydrate moieties of said polysaccharide; wherein the macromolecular product is obtained by any one of the methods described herein.

In certain embodiments, the invention provides a composition in the form of a gel of the biodegradable biocompatible ketal and a biologically active compound disposed within the gel. Alternatively or additionally, a diagnostic label can be disposed within the gel or bound to the gel matrix.

In another embodiment, the invention provides a composition in the form of a solution of the biodegradable biocompatible polyketal and a pharmaceutically useful entity, a drug or a macromolecule dissolved within the solution. Alternatively or additionally, a diagnostic label can be dissolved within the solution.

In certain embodiments, there is provided a composition comprising a biodegradable biocompatible polyketal of the invention associated with an effective amount of a therapeutic agent; wherein the therapeutic agent is incorporated into an released from said biodegradable biocompatible polyketal matrix by degradation of the polymer matrix or diffusion of the agent out of the matrix over a period of time. In certain embodiments, the therapeutic agent is selected from the group consisting of vitamins, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents, and combination thereof.

In variations of these embodiments, it may be desirable to include other pharmaceutically active compounds, such as antiinflammatories or steroids which are used to reduce swelling, antibiotics, antivirals, or antibodies. Other compounds which can be included are preservatives, antioxidants, and fillers, coatings or bulking agents which may also be utilized to alter polymer matrix stability and/or drug release rates.

Additives Used to Alter Properties of Polymeric Compositions:

In a preferred embodiment, only polyketal and drugs to be released are incorporated into the delivery device or construct, although other biocompatible, preferably biodegradable or metabolizable, materials can be included for processing, preservation and other purposes.

Buffers, acids and bases are used to adjust the pH of the composition. Agents to increase the diffusion distance of agents released from the implanted polymer can also be included.

Fillers are water soluble or insoluble materials incorporated into the formulation to add bulk. Types of fillers include sugars, starches and celluloses. The amount of filler in the formulation will typically be in the range of between about 1 and about 90% by weight.

Biodegradable Biocompatible Polyketals—Methods of Use

The present invention encompasses highly regular, biodegradable polymers for use in biomedical applications, primarily (but not exclusively) in the fields of pharmacology, bioengineering, wound healing, and dermatology/cosmetics. In particular, medical applications for the biocompatible biodegradable polymers of the invention include tablet coatings, plasma substitutes, gels, contact lenses, surgical implants, systems for controlled drug release, as ingredients of eyedrops, wound closure applications (sutures, staples), orthopedic fixation devices (pins, rods, screws, tacks, ligaments), dental applications (guided tissue regeneration), cardiovascular applications (stents, grafts), intestinal applications (anastomosis rings), and as long circulating and targeted drugs. Biodegradable biocompatible polyketals of the present invention can be employed as components of biomaterials, drugs, drug carriers, pharmaceutical formulations, medical devices, implants, and can be associated with small molecules, pharmaceutically useful entities, drugs, macromolecules and diagnostic labels.

Methods of Treating

In certain preferred embodiments of the invention, the polyketals are used in methods of treating animals (preferably mammals, most preferably humans). In one embodiment, the polyketals of the present invention may be used in a method of treating animals which comprises administering to the animal the biodegradable biocompatible polyketal. For example, polyketals in accordance with the invention can be administered in the form of soluble linear polymers, copolymers, conjugates, colloids, particles, gels, solid items, fibers, films, etc. Biodegradable biocompatible polyketals of this invention can be used as drug carriers and drug carrier components, in systems of controlled drug release, preparations for low-invasive surgical procedures, etc. Pharmaceutical formulations can be injectable, implantable, etc.

In one embodiment, a method of administering to a patient in need of treatment comprises administering to the subject an effective amount of a suitable therapeutic agent; wherein the therapeutic agent is incorporated into and released from biodegradable biocompatible polyketal matrix by degradation of the polymer matrix or diffusion of the agent out of the matrix over a period of time.

In another embodiment, the therapeutic agent can be locally delivered by implantation of the biodegradable biocompatible polyketal matrix associated with the therapeutic agent.

In yet another embodiment, additional biologically active compounds can be administered with the polymer-associated therapeutic agent. Examples of biologically active compounds include chemotherapeutics, antiinflammatories, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or antithrombotic agents, local anesthetics, ophthalmics, prostaglandins, anti-depressants, anti-psychotic substances, anti-emetics, imaging agents, and combinations thereof.

In one embodiment, a method for treating an animal comprises administering to the animal the biodegradable biocompatible polyketal of the invention as a packing for a surgical wound from which a tumor or growth has been removed. The biodegradable biocompatible polyketal packing will replace the tumor site during recovery and degrade and dissipate as the wound heals.

In certain embodiments, the polyketal is associated with a diagnostic label for in vivo monitoring.

Applications to Drug Delivery Methods

Polyketal—small-molecule-drug conjugates: In one embodiment, pharmaceutical agents are associated with the biodegradable biocompatible polyketal to form a biodegradable biocompatible gel or mass of polyketal in which the drug is entrapped or bound to gel matrix, or a soluble conjugate of a drug and a polyketal. This can be achieved, for example, by coupling the polyketal with a drug (for example, taxol or camptothecin (CPT)). Alternatively, the drug can be entrapped by dissolution of the drug in the presence of the biodegradable biocompatible polyketal during removal of a solvent, or during crosslinking. When soluble ketal-drug conjugates are administered (e.g., injected) into an animal, they can circulate and accumulate at a desirable site, and slowly release the drug either in circulation, or at the accumulation site, either intracellularly or extracellularly. When gels or masses are implanted into an animal, slow hydrolysis of the biodegradable biocompatible polyketal mass or gel occurs with continuous slow release of the agent in the animal at the location where its function is required. Such polymer-drug pharmaceutical compositions may afford release of the physiologically active substance into physiological fluids in vivo over a sustained period (for an example of polymer-drug conjugate, see Li, et al. "Water soluble paclitaxel prodrugs" U.S. Pat. No. 6,262,107, 2001, the entire contents of which are incorporated herein by reference). In addition, the hydrophilic polyketals of the invention may be used to stabilize drugs, as well as to solubilize otherwise insoluble compounds. For example, Paclitaxel, an anti-microtubule agent that has shown a remarkable anti-neoplastic effect in human cancer in Phase I studies and early Phase II and III trials (Horwitz et al., "Taxol, mechanisms of action and resistance," J. Natl. Cancer Inst. Monographs No. 15, pp. 55-61, 1993), has limited solubility in water, which has hampered its development for clinical trial use. The polyketal-drug pharmaceutical compositions of the invention could provide water soluble taxoids to overcome the drawbacks associated with the insolubility of the drugs themselves, and also provide the advantages of accumulation in tumors, targeting to cancer cells and controlled release so that tumors may be eradicated more efficiently. Association of chemotherapeutic drugs to the polyketals of the invention may also be an attractive approach to reduce systemic toxicity and improve the therapeutic index. In particular, it is known in the art that polymers with molecular mass larger than 30 kDa do not readily diffuse through normal capillaries and glomerular endothelium, thus sparing normal tissue from irrelevant drug-mediated toxicity (Maeda and Matsumura, "Tumoritropic and lymphotropic principles of macromolecular drugs", Critical Review in Therapeutic Drug Carrier Systems, 6:193-210, 1989; Reynolds, T., "Polymers help guide cancer drugs to tumor targets-and keep them there," J. Natl. Cancer Institute, 87:1582-1584, 1995). On the other hand, it is well established that malignant tumors often have altered capillary endothelium and greater permeability than normal tissue vasculature (Maeda and Matsumura, 1989; Fidler, et al., "The biology of cancer invasion and metastasis," Adv. Cancer Res., 28:149-250, 1987). Thus, a polymer-drug conjugate, such as those described in the present invention, that would normally remain in the vasculature, may selectively leak from blood vessels into tumors, resulting in tumor accumulation of active therapeutic drug. The methods described herein could also be used to make water soluble polyketal complexes of other therapeutic agents, contrast agents and drugs.

Polyketal-modified proteins: In certain embodiments, the polyketals may be associated to a protein or peptide (for example enzymes or growth factors) to form a polyketal-modified protein/peptide. Improved chemical and genetic methods have made many enzymes, proteins, and other peptides and polypeptides available for use as drugs or biocatalysts having specific catalytic activity. However, limitations exist to the use of these compounds. For example, enzymes that exhibit specific biocatalytic activity sometimes are less useful than they otherwise might be because of problems of low stability and solubility. During in vivo use, many proteins are cleared from circulation too rapidly. Some proteins have less water solubility than is optimal for a therapeutic agent that circulates through the bloodstream. Some proteins give rise to immunological problems when used as therapeutic agents. Immunological problems have been reported from manufactured proteins even where the compound apparently has the same basic structure as the homologous natural product. The use of polymer-modified proteins or peptides may help protect the protein/peptide from chemical attack, limit its adverse side effects when injected into the body, increase its size, and may thus potentially improve its therapeutic profile in vivo (e.g., safety, efficacy and stability in biological media). See for example Harris et al. "Multiarmed, monofunctional, polymer for coupling to molecules and surfaces" U.S. Pat. No. 5,932,462, 1999. Examples of proteins that may be used in this context are enzymes, recognition proteins, carrier proteins, and signaling proteins and polypeptides, such as, urokinase, catalase, hemoglobin, granulocyte colony stimulating factor (G-CSF), interferons, cytokines, leptins, insulin, etc.

Although there is no theory that predicts the optimal composition, size and shape of a macromolecule conjugate, it can be expected that, for some applications, conjugates consisting of one protein molecule and one polyketal molecule will be preferable, whereas in other applications conjugates comprising several identical or different protein or peptide molecules per polyketal molecule can be preferable. In one preferred embodiment, a protein is conjugated with a polyketal of the invention via a terminal group of the latter. In another embodiment, one or more protein or peptide molecules are conjugated to the polyketal molecule of the invention at random points.

Cationized polyketal: In another embodiment, the polyketals of the present invention may find use as a nucleic acid carrier vehicle for delivery of nucleic acid material to target cells in biological systems (for example in applications using adducts with DNA or Polyketal-modified virus). Such material may find applications for in vivo delivery of genes or therapeutic DNA to a patient in carrying out gene therapy or DNA vaccination treatment (See for example Schacht et al. "Delivery of nucleic acid material" U.S. Pat. No. 6,312,727, 2001; German et al. "Enhanced adenovirus-assisted transfection composition and method" U.S. Pat. No. 5,830,730, 1998). For example, the polyketal may be synthesized or modified so as to form a "cationized" material whereby one or more cationic sites are included or incorporated in the polyketal molecule. Association or binding of this cationized hydrophilic polymer with a polyanionic nucleic acid component results in a material that may function as a DNA or nucleic acid delivery device. The nucleic acid component may comprise a polynucleotide, plasmid DNA, linear double-helical DNA, RNA or a virus. In another embodiment, the cationic polyketal core may be associated, directly or indirectly, to other molecular entities or moieties, especially bioactive molecules, that modify the biological and/or physicochemical characteristics of the complex to improve suitability or specificity for use in delivering the nucleic acid material to target cells. These other molecular entities or moieties may comprise cell-receptor targeting moieties and/or other specific bioactive agents providing, for example, membrane disrupting agents, agents capable of promoting endocytic internalization following binding to cell surface molecules, and nuclear-homing agents, useful for facilitating entry and delivery of the nucleic acid material, e.g. DNA, into cells.

Polyketal-modified liposomes: In yet another embodiment, the polyketals of the present invention may be associated with a liposome (see for example Dadey "Polymer-associated liposomes for drug delivery and method of manufacturing the same" U.S. Pat. No. 5,935,599, 1999). In certain embodiments, the polyketal-associated liposome is formulated with a drug or a therapeutic agent to provide a drug composition that treats an underlying disease or complications associated with the disease. The polyketal-associated liposome may be formulated with either water-soluble or water-insoluble drugs, or both. Therefore, a drug composition containing a polyketal-associated liposome and a drug can be administered in a variety of dosage forms. A liposome is a mono- or multilamellar vesicle prepared from a phospholipid or other suitable lipids or mixtures thereof. Structurally, lamellae are bilayer membranes having polar ends of lipids in one layer forming the external surface of the spherical membrane and the polar ends of lipids in a second layer forming the internal surface of the spherical membrane. Membranes can include hydrophobic additives, such as cholesterol. The nonpolar, hydrophobic tails of the lipids in the two layers self-assemble to form the interior of the bilayer membrane. Liposomes can microencapsulate compounds, and transport the compounds through environments wherein they are normally degraded. The liposome can be prepared by conventional techniques from phosphatidylethanolamine, phosphatidylcholine, phosphatidylserine, phosphatidylinositol, phostidylglycerol, sphingomyelin, and mixtures thereof. The outer layer of a liposome can be modified with a polyketal to either prevent liposome aggregation, or to prolong liposome circulation in blood, or for other purposes. Preferably, polyketal molecules are chemically linked to lipid molecules constituting the outer membrane. Some or all polyketal molecules can be further modified with targeting moieties that assist liposome binding to target cells or tissues. In a preferred embodiment, polyketal molecules are linked to lipid molecules through terminal groups, forming lipid-polyketal conjugates. The latter can be incorporated into liposomes during the process of liposome formation, e.g. by extrusion. Alternatively, polyketals can be chemically bound to pre-formed liposomes comprising suitable functional groups on the outer surface (e.g., amino, mercapto, or carboxygroups).

Polyketal-modified nano- and microparticles: In a further embodiment of the present invention, the polyketals may be designed so as to have properties suitable for manufacturing by various processes into nanoparticles, microparticles and microspheres for applications in drug delivery systems. Polyketals can be utilized in such applications as interface components, particle matrix components, or both. Where polyketals are used as interface components, the (inner) particle can be a nanoparticle (e.g., iron oxide nanocrystal or combination thereof), a latex particle (e.g., polystyrene nanosphere or microsphere), a gel particle (e.g., crosslinked polyketal or polysaccharide gel sphere), etc. Where the polyketal is used as a matrix component, alone or along with other macromolecular components or particulates, the polyketal molecules can be chemically crosslinked or non-chemically associated to form a gel or a solid, and can be chemically or physically associated with a drug. The latter becomes, therefore, incorporated or entrapped in the particle, and can subsequently be released via diffusion or degradation mechanisms.

The slow-release characteristic of the polymer microparticles may also have use in the field of pharmacology where the microparticles can be used, for example, to deliver pharmacological agents in a slow and continual manner (see for example Sokoll et al. "Biodegradable targetable microparticle delivery system" U.S. Pat. No. 6,312,732, 2001). A wide range of drugs such as anti-hypertensives, analgesics, steroids and antibiotics can be used in accordance with the present invention to provide a slow release drug delivery system. Large molecules, such as proteins, can also be entrapped in micro- and nanoparticles, using methods of particle formation that do not inactivate the large molecule. Microspheres may be prepared by known methods in the art, for example, using a single emulsification process (U.S. Pat. No. 4,389,330 to Tice et al.; U.S. Pat. No. 3,691,090 to Kitajima et al.), a double emulsification process (Edwards et al., Science 276: 1868-1871, 1997), a phase inversion microencapsulation process (Mathiowitz et al., Nature 386: 410-413, 1997), or an atomization-freeze process (Putney and Burke, Nature Biotechnology 16: 153-157, 1998). In the single emulsification process, a volatile organic solvent phase containing a biodegradable polymer, an aqueous solution containing an emulsifier such as polyvinyl alcohol, and a physiologically active substance are homogenized to produce an emulsion. The solvent is evaporated and the resulting hardened microspheres are freeze-dried. In the double emulsification process, an aqueous solution which may contain a physiologically active substance and a volatile organic solvent phase containing a biodegradable polymer are homogenized to form an emulsion. The emulsion is mixed with another aqueous solution, which contains an emulsifier such as polyvinyl alcohol. Evaporation of the solvent and freeze-drying produces microspheres. In the phase inversion microencapsulation process, the drug is added to a dilute polymer solution in a solvent (e.g. dichloromethane) which is then poured rapidly into an unstirred bath of another liquid (e.g. petroleum ether) causing nano- and microspheres to form spontaneously. In the atomization-freeze process, the micronized solid physiologically active substance is suspended in a solvent phase containing a biodegradable polymer that is then atomized using sonication or air-atomization. This produces droplets that are then frozen in liquid nitrogen. Addition of another solvent in which both the polymer and the drug are insoluble extracts the solvent from the microspheres. In such processes, polyketals can be used as interface components formed during or after particle formation. Preferably, the process is engineered such that polyketal molecules form a monolayer on the particle surface, which is dense enough to modify the particle surface hydrophilicity, and/or to prevent direct contact of cells and/or recognition proteins with the particle surface. This can be achieved, for example, by chemical coupling of the polyketal to the surface of the pore-formed particles, or through addition of polyketal-matrix polymer conjugates into technological solutions. Such conjugates (e.g., block copolymers) will, in appropriately optimized conditions, incorporate into particles such that the matrix polymer block will incorporate into the particle body, while the polyketal block will be exposed on the particle surface. Similar approaches can be used for the modification of inorganic particles (such as colloids and nanocrystals) with ketals during or after their formation. Polyketals can be attached to the surfaces of such particles either chemically (conjugation or grafting) or physically (adsorption). A further description of polyketal use as an interface component is given in one of the following sections.

In another embodiment, the biodegradable biocompatible polyketals of the present invention can be monitored in vivo by suitable diagnostic procedures. Such diagnostic procedures include nuclear magnetic resonance imaging (NMR), magnetic resonance imaging (MRI), ultrasound, X-ray, scintigraphy, positron emission tomography (PET), etc. The diagnostic procedure can detect, for example, polyketal disposition (e.g., distribution, localization, density, etc.) or the release of drugs, prodrugs, biologically active compounds or diagnostic labels from the biodegradable biocompatible polyketals over a period of time. Suitability of the method largely depends on the form of the administered polyketal and the presence of detectable labels. For example, the size and shape of polyketal implants can be determined non-invasively by NMR imaging, ultrasound tomography, or X-ray ("computed") tomography. Distribution of soluble polyketal preparation comprising a gamma emitting or positron emitting radiotracer can be performed using gamma scintigraphy or PET, respectively. Microdistribution of polyketal preparation comprising a fluorescent label can be investigated using photoimaging.

It is understood, for the purpose of this invention, that transfer and disposition of polyketals in vivo can be regulated by modifying groups incorporated into the polyketal structure or conjugated with the polyketal, such as hydrophobic and hydrophilic modifiers, charge modifiers, receptor ligands, antibodies, etc. Such modification, in combination with incorporation of diagnostic labels, can be used for development of new useful diagnostic agents. The latter can be designed on a rational basis (e.g., conjugates of large or small molecules binding known tissue components, such as cell receptors, surface antigens, etc.), as well as through screening of libraries of polyketal molecules modified with a variety of moieties with unknown or poorly known binding activities, such as synthetic peptides and oligonucleotides, small organic and metalloorganic molecules, etc.

Interface Component

In one embodiment of the present invention, the biodegradable biocompatible polyketal can be used as an interface component. The term "interface component" as used herein, means a component, such as a coating or a layer on an object, to alter the character of object interaction with biological interaction with biological milieu, for example, to suppress foreign body reactions, decrease inflammatory response, suppress clot formation, etc. It should be understood that the object can be microscopic or macroscopic. Examples of microscopic objects include macromolecules, colloids, vesicles, liposomes, emulsions, gas bubbles, nanocrystals, etc. Examples of macroscopic objects include surfaces, such as surfaces of surgical equipment, test tubes, perfusion tubes, items contacting biological tissues, etc. It is believed that interface components can, for example, provide the object protection from direct interactions with cells and opsonins and, thus, to decrease the interactions of the object with the biological system.

Surfaces can be modified by the biodegradable biocompatible polyketals of the present invention by, for example, conjugating functional groups of the biodegradable biocompatible polyketals with functional groups present on the surface to be modified. For example, aldehyde groups of the biodegradable biocompatible polyketal precursors can be linked with amino groups by employing reducing agents or isocyanides. Alternatively, carboxyl groups of the biodegradable biocompatible polyketals can be conjugated with amino, hydroxy, sulphur-containing groups, etc. In another embodiment, a biodegradable biocompatible polyketal of the invention which includes a suitable terminal group can be synthesized, such as a polyalcohol having a terminal carboxylic group. A polymer can be connected to a surface by reaction of the terminal group. Examples of suitable polymers include those formed, for example, by oxidation of a reducing-end acetal group into a carboxyl group, such as by using iodine or bromine. The remainder of the polysaccharide is then oxidized by employing an effective amount of a glycol-specific oxidizing agent to form an aldehyde. The aldehydes can be selectively modified by, for example, reduction into hydroxyl groups. The resulting polymer will generally have one terminal carboxyl group that can be used for one-point modification, such as by employing a carbodiimide.

In still another embodiment, a suitable polysaccharide can be linked with a surface by reaction of a reducing or non-reducing end of the polysaccharide or otherwise, by subsequent oxidation and further conversion of the remainder of the polysaccharide to produce a polyketal.

It is to be understood that the biodegradable biocompatible polyketals of this invention can be conjugated with macromolecules, such as enzymes, polypeptides, proteins, etc., by the methods described above for conjugating the biodegradable biocompatible polyketals with functional groups present on a surface.

The biodegradable biocompatible polyketals of the invention can also be conjugated with a compound that can physically attach to a surface via, for example, hydrophobic, van der Waals, and electrostatic interactions. For example, the biodegradable biocompatible polyketal precursors can be conjugated with lipids, polyelectrolytes, proteins, antibodies, lectins, etc.

It is believed that interface components can prolong circulation of macromolecular and colloidal drug carriers. Therefore, small molecules, biologically active compounds, diagnostic labels, etc., being incorporated in such carriers, can circulate throughout the body without stimulating an immunogenic response and without significant interactions with cell receptors and recognition proteins (opsonins). Further, interface components can be used to modify surfaces of implants, catheters, etc. In other embodiments of the present invention, biomedical preparations of the biodegradable biocompatible polyketal can be made in various forms. Examples include implants, fibers, films, etc.

Chiral Polyketals

Other aspects of the present invention pertain to methods and compositions useful in separations of stereoisomers.

The so-called "three point rule" is a commonly used rule-of-thumb in many chiral recognition strategies. The "three point rule" recommends that there be a minimum of three simultaneous interactions between the chiral recognition medium and at least one of the enantiomers to be separated. In addition, at least one of the three interactions must be stereochemically dependent. The three interactions need not be attractive interactions, and may for example employ repulsion due to steric effects.

The three-point rule is satisfied by the novel chiral polyketals of the present invention, which have at least three functional groups that can yield different chiral environments: (1) the chiral center(s) in the polysaccharide backbone; (2) the stereoregular isotactic form of that backbone; and (3) the pendent functional groups such as carbonyl, carboxyl, or hydroxyl, including hydrophobic interactions with side chains.

If desired, the novel polymers may be readily crosslinked, without disrupting the polymer backbone ketal links, generating stable, solvent-swollen, gels. The novel polymers may be used as a stationary-phase or pseudo-stationary phase in separation techniques such as high performance liquid chromatography or electrokinetic capillary chromatography. The polymers are either water-soluble or they swell in aqueous media, and are particularly useful in separations of stereoisomers (enantiomers or diastereomers).

Chiral Polyketals

In a preferred embodiment, the polyketals of the present invention are chiral and comprise repeat structural units, wherein substantially all the structural units comprise (i) at least one ketal group wherein at least one ketal oxygen atom is within the polymer main chain; and (ii) at least one chiral group.

In a certain embodiment, at least a subset of the repeat structural units have the following structure:

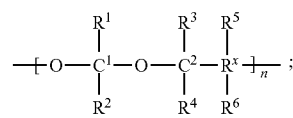

wherein each occurrence of $R^1$ and $R^2$ is an organic moiety and includes a carbon atom or heteroatom covalently attached to $C^1$. $R^x$ includes a carbon atom covalently attached to $C^2$. n is an integer. Each occurrence of $R^3$, $R^4$, $R^5$ and $R^6$ is independently hydrogen or an organic moiety; and for each occurrence of the bracketed structure n, at least one of $C^1$, $C^2$, $R^x$, $R^1$, $R^2$, $R^3$, $R^4$, $R^5$ and $R^6$ is chiral.

In another embodiment of the invention, at least a subset of the repeat structural units have the following structure:

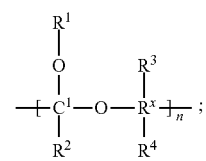

wherein each occurrence of $R^2$ is an organic moiety and includes a carbon atom or heteroatom covalently attached to $C^1$; $R^x$ includes a carbon atom covalently attached to $C^1$; n is an integer; each occurrence of $R^1$ is an organic moiety; each occurrence of $R^3$ and $R^4$ is independently hydrogen or an organic moiety; and, for each occurrence of the bracketed structure n, at least one of $C^1$, $C^2$, $R^x$, $R^1$, $R^2$, $R^3$ and $R^4$ is chiral.

Each occurrence of $R^1$, $R^2$, $R^3$, $R^4$, $R^5$ and $R^6$ may be independently hydrophobic or hydrophilic, and may be the same or different throughout the polymer. Examples of organic moieties which are suitable include (but are not limited to) branched and unbranched alkyl, alkenyl, alkynyl, haloalkyl, acyl, aryl, alkylaryl, heterocyclic group, heteroaryl, alkoxy, mercaptoalkyl, amino, alkylamino, dialkylamino, trialkylamino, cyano, hydroxy, halo, mercapto, nitro, carboxyaldehyde, carboxy, alkoxycarbonyl, carboxamide, carbamates, sulfonyl, sulfoxyl, and phosphate moieties.

In a preferred embodiment of the present invention, the chiral polyketals comprise the structure:

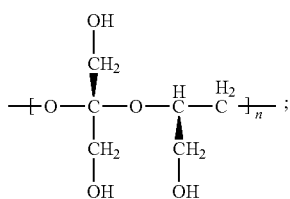

or are direct derivatives thereof, obtained by replacement of some or all OH or $CH_2OH$ groups with other suitable groups.

In another preferred embodiment, the chiral polyketal of the invention comprise the structure:

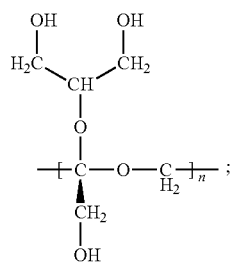

wherein n is an integer, or are direct derivatives thereof, obtained by replacement of some or all OH or $CH_2OH$ groups with other suitable groups.

In yet another embodiment, the chiral polyketals of the invention can be crosslinked. A suitable crosslinking agent has the formula $X^1$—(R)—$X^2$, where R is a spacer group and $X^1$ and $X^2$ are reactive groups. The spacer group R may be an aliphatic, alicyclic, heteroaliphatic, heteroalicyclic, aryl or heteroaryl moiety. Examples of suitable spacer groups include biodegradable or nonbiodegradable groups, for example, aliphatic groups, carbon chains containing biodegradable inserts such as disulfides, esters, etc. The term "reactive group," as it relates to $X^1$ and $X^2$, means functional groups which can be connected by a reaction within the chiral polyketals, thereby crosslinking the chiral polyketals. Suitable reactive groups which form crosslinked networks with the chiral polyketals include epoxides, halides, tosylates, mesylates, carboxylates, aziridines, cyclopropanes, esters, N-oxysuccinimide esters, disulfides, anhydrides, substituted hydroxylamines, hydrazines, hydrazides, etc.

Alternatively, the term "reactive" group as it relates to $X^1$ and $X^2$ means a nucleophilic group that can be reacted with an aldehyde intermediate of the chiral polyketals, thereby crosslinking the chiral polyketals. Suitable reactive groups for the aldehyde intermediate include amines, thiols, polyols, alcohols, ketones, aldehydes, diazocompounds, boron derivatives, ylides, isonitriles, hydrazines and their derivatives and hydroxylamines and their derivatives, etc.

In one embodiment of the present invention, the chiral polyketals are bonded to a solid support, which imparts them improved properties. For example, the resistance of chiral stationary phases to pressure is important for their use in practice, since high flow rates are necessary to achieve high space/time yields in the chromatographic splitting of racemates. If the resistance to pressure is not adequate, these flow rates lead to blocking of the columns. Chiral phases which are stable to pressure are obtained when the optically active material is immobilized on an inorganic support material. Silica gels are as a rule used as inorganic support materials. The chiral polymers can be absorbed onto these silica gels, for example, by being adsorbed physically or fixed covalently.

One embodiment of the present invention provides chiral stationary chromatography phases comprising an inorganic support material and the chiral polyketal of the invention which is bonded to said support material either directly or via a spacer grouping. Examples of suitable solid supports are those containing reactive groups on the surface; said reactive groups being capable of reacting with certain functional groups on the chiral polyketal, thus effecting covalent conjugation of the chiral polymer on the solid support. Examples of suitable reactive groups include hydroxyl, amino or sulfhydryl groups, or combination thereof. In one embodiment of the invention, prior to conjugation with the chiral polyketal, the solid support is chemically modified so as to coat its surface with reactive groups suitable for reaction with said chiral polyketal.

In one embodiment of the invention, the chiral polyketal is associated with a macromolecule for applications in affinity chromatography. Examples of macromolecules include, but are not limited to, receptors, enzymes, proteins and antibodies.

In one embodiment, the chiral polyketal of the invention is not 100% optically pure. Chromatography is a multi-step method where the separation is a result of the sum of a large number of interactions. This allows for diminished requirements for the enantioselectivity of the stationary phase, whereby if the polyketal stationary phase contains a small quantity of the wrong isomer the effect will be countered by the combined action of the adsorbtions along the column as a whole. It is possible to achieve resolutions on chiral stationary phases that are somewhat less than 100% pure. Decreasing the purity of the stationary phase will simply decrease the enantioselectivity of the column.

Chiral Polyketals—Methods of Preparation

According to the present invention, any available techniques can be used to make the inventive chiral polyketals or compositions including them. For example, semi-synthetic and fully synthetic methods such as those discussed in detail below may be used.

Semi-Synthetic Route

In a preferred embodiment, a method for forming the chiral polyketals of the present invention comprises a process by which a suitable polysaccharide is combined with an effective amount of a glycol-specific oxidizing agent to form an aldehyde intermediate. The aldehyde intermediate is then reacted with a suitable reagent to form a chiral polyketal comprise repeat structural units, wherein substantially all the structural units comprise (i) at least one ketal group wherein at least one ketal oxygen atom is within the polymer main chain; and (ii) at least one chiral group.

In certain embodiments, there is provided a method for preparing a chiral polymer, said method comprising steps of: a) reacting an effective amount of an oxidizing agent with a polysaccharide to form a polyketal aldehyde; b) optionally treating the polyketal aldehyde with a suitable reagent under suitable conditions to form a polyketal; and c) optionally repeating step b) until the desired functionalization of said polyketal is achieved; thereby forming a chiral polymer, wherein said polymer comprises repeat structural units, wherein substantially all the structural units comprise: i) at least one ketal group wherein at least one ketal oxygen atom is within the polymer main chain; and ii) at least one chiral group.

In certain embodiments, the method for preparing a chiral polymer, comprises steps of: a) reacting an effective amount of an oxidizing agent with a polysaccharide to form a polyketal aldehyde; b) optionally treating the polyketal aldehyde with a suitable reagent to form a polyketal intermediate;

c) optionally repeating step b) until the desired functionalization of said polyketal intermediate is achieved; and d) reacting said polyketal intermediate with a suitable chiral reagent; thereby forming a chiral polymer, wherein said polymer comprises repeat structural units, wherein substantially all the structural units comprise: i) at least one ketal group wherein at least one ketal oxygen atom is within the polymer main chain; and ii) at least one chiral group.

In a certain embodiment, at least a subset of the repeat structural units have the following structure:

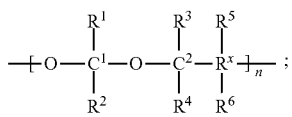

wherein each occurrence of $R^1$ and $R^2$ is an organic moiety and includes a carbon atom or heteroatom covalently attached to $C^1$. $R^x$ includes a carbon atom covalently attached to $C^2$. n is an integer. Each occurrence of $R^3$, $R^4$, $R^5$ and $R^6$ is independently hydrogen or an organic moiety; and for each occurrence of the bracketed structure n, at least one of $C^1$, $C^2$, $R^1$, $R^2$, $R^3$, $R^4$, $R^5$ and $R^6$ is chiral.

In another embodiment of the invention, at least a subset of the repeat structural units have the following structure:

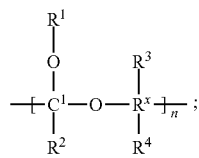

wherein each occurrence of $R^2$ is an organic moiety and includes a carbon atom or heteroatom covalently attached to $C^1$; $R^x$ includes a carbon atom covalently attached to $C^1$; n is an integer; each occurrence of $R^1$ is an organic moiety; each occurrence of $R^3$ and $R^4$ is independently hydrogen or an organic moiety; and, for each occurrence of the bracketed structure n, at least one of $C^1$, $C^2$, $R^x$, $R^1$, $R^2$, $R^3$ and $R^4$ is chiral.

Each occurrence of $R^1$, $R^2$, $R^3$, $R^4$, $R^5$ and $R^6$ may be hydrophobic or hydrophilic, and may be the same or different throughout the polymer. Examples of organic moieties which are suitable include (but are not limited to) branched and unbranched alkyl, alkenyl, alkynyl, haloalkyl, acyl, aryl, alkylaryl, heterocyclic group, heteroaryl, alkoxy, mercaptoalkyl, amino, alkylamino, dialkylamino, trialkylamino, cyano, hydroxy, halo, mercapto, nitro, carboxyaldehyde, carboxy, alkoxycarbonyl, carboxamide, carbamates, sulfonyl, sulfoxyl, and phosphate moieties.

In a preferred embodiment of the present invention, the chiral polyketals comprise the structure:

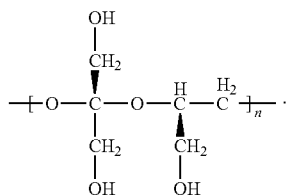

In another preferred embodiment, the chiral polyketal of the invention comprise the structure:

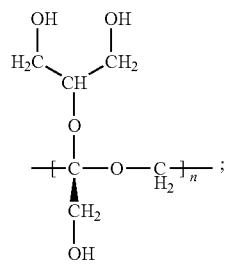

wherein n is an integer.

In yet another embodiment, the chiral polyketals of the present invention can form linear or branched structures, and can have substitutents selected from the group consisting of branched and unbranched alkyl, alkenyl, alkynyl, haloalkyl, acyl, aryl, alkylaryl, heterocyclic group, heteroaryl, alkoxy, mercaptoalkyl, amino, alkylamino, dialkylamino, trialkylamino, cyano, hydroxy, halo, mercapto, nitro, carboxyaldehyde, carboxy, alkoxycarbonyl, carboxamide, carbamates, sulfonyl, sulfoxyl, and phosphate moieties.

Structure, yield and molecular weight of the resultant polyaldehyde depend on the initial polysaccharide. Polysaccharides that do not undergo significant depolymerization in the presence of glycol-specific oxidizing agents, for example, poly (2,1) and (2,6) fructoses, are preferable. Examples of suitable polysaccharides include alpha and beta 2,1 and 2,6 fructans. Particularly preferred polysaccharides are Inulin, Levans from plants, and bacterial fructans. Examples of suitable glycol-specific oxidizing agents include sodium periodate, lead tetra-acetate, periodic acid, etc. In certain embodiments, the oxidation system consists of a non-specific oxidizing agent in combination with glycol-specific catalyst or and intermediate oxidizer. Examples of suitable reducing agents include sodium borohydride, sodium cyanoborohydride, etc. Temperature, pH and reaction duration can affect the reaction rate and polymer hydrolysis rate. The reaction is preferably conducted in the absence of light. One skilled in the art can optimize the reaction conditions to obtain polymers of desired composition. The resultant polymeric aldehyde intermediate may be reduced to the corresponding alcohol via a suitable reducing agent. Alternatively, aldehyde groups can be conjugated with a variety of compounds or converted to other types of functional groups. In another embodiment, the precursor carbohydrate has a chiral atom outside of the cleavage site. Thus the chirality of that atom is retained, and the polyketal is chiral or optically active.

In certain embodiments, the polyketals of the present invention can contain intermittent irregularities throughout the polyketal, such as incompletely oxidized saccharide moieties or additional groups in the main chain or in the side chains.

Since it is believed that oxidation does not affect configurations at $C^1$ and $C^2$, the aldehyde intermediate and the polyketal retain the configuration of the parent polysaccharide and the polyketal is formed in stereoregular isotactic forms.

Fully Synthetic Route

In another preferred embodiment, the chiral polyketals of the present invention can be formed by combining a suitable initiator with a chiral precursor compound comprising the chemical structure:

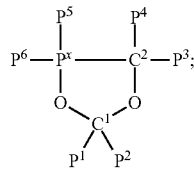

which forms a chiral polymer intermediate comprising the chemical structure:

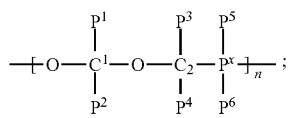

wherein each occurrence of $P^1$ and $P^2$ includes a carbon atom covalently attached to $C^1$ and is independently an organic moiety or a protected organic moiety; $P^x$ includes a carbon atom covalently attached to $C^2$; n is an integer; each occurrence of $P^3$, $P^4$, $P^5$ and $P^6$ is independently hydrogen, an organic moiety or a protected organic moiety. For each occurrence of the bracketed structure n, at least one of $C^1$, $C^2$, $P^x$, $P^1$, $P^2$, $P^3$, $P^4$, $P^5$ and $P^6$ is chiral. In a preferred embodiment, $P^1$, $P^2$, $P^3$, $P^4$, $P^5$ and $P^6$ do not prevent polymerization. In one embodiment, when appropriate, the protected organic moieties of the polymer intermediate are deprotected and optionally derivatized, thereby forming the polyketal comprising the structure:

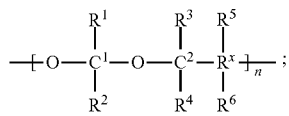

wherein each occurrence of $R^1$ and $R^2$ is an organic moiety and includes a carbon atom covalently attached to $C^1$; $R^x$ includes a carbon atom covalently attached to $C^2$; n is an integer; each occurrence of $R^3$, $R^4$, $R^5$ and $R^6$ is independently hydrogen or an organic moiety; and, for each occurrence of the bracketed structure n, at least one of $C^1$, $C^2$, $R^x$, $R^1$, $R^2$, $R^3$, $R^4$, $R^5$ and $R^6$ is chiral. Alternatively, other ring opening techniques can be employed or developed, for example employing appropriate catalysts and resulting in the formation of polyketals comprising unsaturated linkages within the main chain. The latter can be further transformed into single bonds using appropriate reagents. Thus, in certain embodiments, a method for forming a chiral polymer comprises steps of: a) reacting a suitable initiator with a compound having the chemical structure:

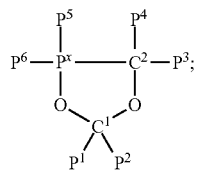

thereby forming a polymer intermediate comprising the chemical structure:

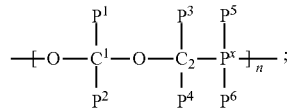

wherein each occurrence of $P^1$ and $P^2$ is independently an organic moiety or a protected organic moiety and includes a carbon atom covalently attached to $C^1$; each occurrence of $P^x$ is independently an organic moiety and includes a carbon atom covalently attached to $C^2$; n is an integer; each occurrence of $P^3$, $P^4$, $P^5$ and $P^6$ is independently hydrogen, an organic moiety or a protected organic moiety; and for each occurrence of the bracketed structure n, at least one of $C^1$, $C^2$, $P^x$, $P^1$, $P^2$, $P^3$, $P^4$, $P^5$ and $P^6$ is chiral; thereby forming a first polyketal intermediate; b) optionally reacting said first polymer intermediate with a suitable reagent to form a second polyketal intermediate; and c) optionally repeating step b) until the desired functionalization of said polyketal intermediate is achieved; thereby forming a polyketal comprising the structure having the structure:

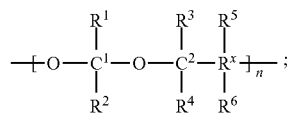

wherein each occurrence of $R^1$ and $R^2$ is independently an organic moiety and includes a carbon atom covalently attached to $C^1$; each occurrence of $R^x$ includes a carbon atom covalently attached to $C^2$; n is an integer; each occurrence of $R^3$, $R^4$, $R^5$ and $R^6$ is independently hydrogen or an organic moiety; and for each occurrence of the bracketed structure n, at least one of $C^1$, $C^2$, $R^x$, $R^1$, $R^2$, $R^3$ and $R^4$ is chiral.

In certain other embodiments, the method for forming a chiral polymer comprises steps of: a) reacting a suitable initiator with a compound having the chemical structure:

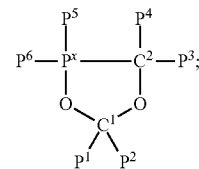

thereby forming a polymer intermediate comprising the chemical structure:

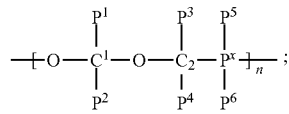

wherein each occurrence of $P^1$ and $P^2$ is independently an organic moiety or a protected organic moiety and includes a carbon atom covalently attached to $C^1$; each occurrence of $P^x$ is independently an organic moiety and includes a carbon atom covalently attached to $C^2$; n is an integer; each occurrence of $P^3$, $P^4$, $P^5$ and $P^6$ is independently hydrogen, an organic moiety or a protected organic moiety; and for each occurrence of the bracketed structure n, at least one of $C^1$, $C^2$, $P^x$, $P^1$, $P^2$, $P^3$, $P^4$, $P^5$ and $P^6$ is chiral; thereby forming a first polyketal intermediate; b) optionally reacting said first polymer intermediate with a suitable reagent to form a second polyketal intermediate; and c) optionally repeating step b) until the desired functionalization of said polyketal intermediate is achieved; thereby forming a polyketal comprising the structure having the structure:

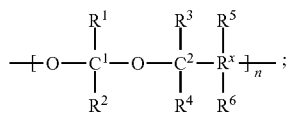

wherein each occurrence of $R^1$ and $R^2$ is independently an organic moiety and includes a carbon atom covalently attached to $C^1$; each occurrence of $R^x$ includes a carbon atom covalently attached to $C^2$; n is an integer; each occurrence of $R^3$, $R^4$, $R^5$ and $R^6$ is independently hydrogen or an organic moiety; and for each occurrence of the bracketed structure n, at least one of $C^1$, $C^2$, $R^x$, $R^1$, $R^2$, $R^3$ and $R^4$ is chiral.

"Protected organic moiety," as that term is used herein, means a chemical group which will not interfere with decyclization of the precursor compound by the initiator or prevent subsequent polymerization, and which, upon additional treatment by a suitable agent, can be converted to an organic moiety. Examples of suitable organic moieties include, but are not limited to, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters, polythioesters, pharmaceutically useful groups, a biologically active substance or a diagnostic label.

Each occurrence of $R^1$, $R^2$, $R^3$, $R^4$, $R^5$ and $R^6$ may be hydrophobic or hydrophilic, and may be the same as or different than $P^1$, $P^2$, $P^3$, $P^4$, $P^5$ and $P^6$, respectively.

In another embodiment of the invention, $C^1$, $C^2$, $P^x$, $P^1$, $P^2$, $P^3$, $P^4$, $P^5$ and $P^6$ are not chiral, and the method of preparing the polyketal includes a step whereby the polymer intermediate is reacted with a suitable chiral reagent to form a chiral polyketal (e.g., at least one of $R^1$, $R^2$, $R^3$, $R^4$, $R^5$ and $R^6$ is chiral).

In another embodiment, the resultant chiral polyketal can be chemically modified by, for example, crosslinking the polyketals to form a gel. The crosslink density of the chiral polyketal is generally determined by the number of reactive groups in the polyketal and by the number of crosslinking molecules, and can be controlled by varying the ratio of polyketal to the amount of crosslinker present.

In one embodiment, a suitable crosslinking agent has the formula $X^1$—(R)—$X^2$, where R is a spacer group and $X^1$ and $X^2$ are reactive groups. $X^1$ and $X^2$ may be the same or different. The spacer group R may be an aliphatic, alicyclic, heteroaliphatic, heteroalicyclic, aryl or heteroaryl moiety. Examples of suitable spacer groups include biodegradable or nonbiodegradable groups, for example, aliphatic groups, carbon chains containing biodegradable inserts such as disulfides, esters, etc. The term "reactive group," as it relates to $X^1$ and $X^2$, means functional groups which can be connected by a reaction within the polyketals, thereby crosslinking the chiral polyketals. Suitable reactive groups which form crosslinked networks with the chiral polyketals include epoxides, halides, tosylates, mesylates, carboxylates, aziridines, cyclopropanes, esters, N-oxysuccinimide esters, disulfides, anhydrides etc.

Alternatively, the term "reactive" group as it relates to $X^1$ and $X^2$ means a nucleophilic group that can be reacted with an aldehyde intermediate of the chiral polyketals, thereby crosslinking said chiral polyketals. Suitable reactive groups for the aldehyde intermediate include amines, thiols, polyols, alcohols, ketones, aldehydes, diazocompounds, boron derivatives, ylides, isonitriles, hydrazines and their derivatives and hydroxylamines and their derivatives, etc.

In yet another embodiment, the chiral polyketals of this invention can have a variety of functional groups. For example, aldehyde groups of an intermediate product of polysaccharide oxidation can be converted not only into alcohol groups, but also into amines, thioacetals, carboxylic acids, amides, esters, thioesters, etc.

In certain embodiments, terminal groups of the polymers of this invention can differ from $R^1$, $R^2$, $R^3$, $R^4$, $R^5$ or $R^6$. Terminal groups can be created, for example, by selective modification of each reducing and non-reducing terminal unit of the precursor polysaccharide. One skilled in the art can utilize known chemical reactions to obtain desired products with varying terminal groups. For example, a hemiketal group at the reducing end of a polyketose can be readily and selectively transformed into a carboxylic acid group (e.g., via formation of a carboxyl-substituted glycoside) and further into a variety of other functional groups.

In one embodiment, the terminal group is such that it allows binding of the polymeric chain to a solid support either directly or via a suitable linker. This has the advantage of allowing solid phase chemical modification of the immobilized polymer to the desired chiral polyketal of the invention. Benefits of this technique include ease of purification by filtration, use of excess reagent for driving reactions to completion, and ease of automation. Examples of suitable solid support are polystyrene, polyethylene glycol, cellulose, controlled pore-glass, etc. . . . Examples of suitable linkers are those that can be cleaved under neutral or basic conditions, such as ester or sulfide linkages.

In another embodiment of the invention, the chiral polyketal is associated with a macromolecule for applications in affinity chromatography. Examples of macromolecules include, but are not limited to, receptors, enzymes, proteins and antibodies.

In certain embodiments, there is provided a composition comprising a chiral polyketal; wherein said chiral polyketal is the macromolecular product of the lateral cleavage of a polysaccharide; whereby at least one carbon-carbon bond is cleaved in substantially all the carbohydrate moieties of said polysaccharide. In certain other embodiments, the cleavage is effected using an oxidizing agent. In yet other embodiments, the oxidizing agent is a glycol-specific agent. In still other embodiments, the glycol-specific agent is sodium periodate. In a further embodiment, the oxidizing agent is non-specific and is used in combination with a glycol-specific catalyst.

In certain embodiments, the compositions provided herein comprise a chiral polyketal; wherein said chiral polyketal is the macromolecular product of the lateral cleavage of a polysaccharide; whereby at least one carbon-carbon bond is cleaved in substantially all the carbohydrate moieties of said polysaccharide; wherein said macromolecular product is obtained by any one of the methods described herein.

Chiral Polyketals—Applications to Chromatographic Methods

In another aspect of the present invention, chiral polyketals in accordance with the invention may be used in liquid chromatography, for example as part of the mobile phase in a reversed-phase system employing a C-18 column. Especially in chromatographic systems, chiral polymers in accordance with the present invention may be used on a preparative scale to purify large quantities of racemic mixtures.

In chromatographic applications, chiral polyketals in accordance with the present invention may be present in the mobile phase, or they could instead be incorporated into chiral stationary phases such as gels, wall coatings, and packed columns and capillaries through means known in the art. For example, a gas chromatography capillary column may be packed with silica particles that have been coated with the chiral polymer. Another possibility is the combination of a chiral mobile phase incorporating the chiral polymer in accordance with the present invention, with a different chiral stationary phase. This combination can result in separation efficiencies that are greater than the sum of the parts.

The invention further encompasses the use of the chiral stationary phases according to the invention for the separation of optical isomers, in particular of racemic mixtures into the optical antipodes. The composition of the mobile phase can be chosen and optimized in the customary manner, according to the nature and property of the racemate to be separated. Where a particular set of conditions results in the separation of two enantiomers, then the same or similar conditions should, in general, also successfully separate homologues of those enantiomers, as well as other enantiomers with similar structures. Thus the chiral polyketals of the invention may find use in chromatographic method development. In certain embodiments, the chiral polyketals of the invention are utilized for the separation of optical isomers.

When the polyketal is associated with a macromolecule (for example, receptors, enzymes, proteins, antibodies and the like), the invention encompasses applications in affinity chromatography (e.g., chromatographic techniques that revolve around compound-dependent "specific binding" as a way to differentiate two or more compounds in a test solution). Specific binding is, for example, the affinity exhibited between a receptor molecule and a compound wherein the receptor molecule includes a defined binding locus that discriminatorily binds those compounds which have a predetermined chemical structure. Compounds not having the predetermined chemical structure do not bind with the binding site of the receptor molecule.

Chiral Polyketals—Source for Chiral Compounds

In one embodiment, the chiral polyketals of the present invention constitute an alternative source for chiral compounds.

Due to the wide variety of the substitutents ($R^1$-$R^6$) that can be used, the chemical properties of the polyketals described in the present invention can be modified with great versatility, and thus can be optimized for a particular application. In particular, they can allow access to a wide variety of chiral compounds useful for asymmetric synthesis.

In one embodiment, depolymerization (e.g., hydrolysis, acidolysis or enzymatic degradation) of the polyketals of the present invention will result in the monomeric components ketones and alcohols, or in hydroxyketones. The ketones and hydroxyketones may further isomerize, e.g., to the corresponding hydroxyaldehydes, depending on their structure. These monomeric components can be used as chiral starting material for various enantiomeric syntheses. Furthermore, said monomeric components can be "custom-designed" by suitable chemical modifications of the parent polyketal. In a preferred embodiment, ketone derivatives are generated without isomerization via depolymerization of protected hydrophilic polyketals in non-aqueous media.

Thus the invention encompasses chiral compounds, wherein said compounds are the depolymerization product of the chiral polyketal of the invention. In certain embodiments, the inventive chiral compounds are derived from the depolymerization of a chiral polyketal of the invention; wherein said chiral polyketal is prepared by any one of the methods described herein.

Throughput this document, various publications are referred to, each of which is hereby incorporated by reference in its entirety in an effort to more fully describe the state of the art to which the invention pertains.

The invention will now be further and specifically described by the following examples. All parts and percentages are by weight unless otherwise stated.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The practitioner has a well-established literature of polymer chemistry to draw upon, in combination with the information contained herein, for guidance on synthetic strategies, protecting groups, and other materials and methods useful for the synthesis of the polyketals of this invention.

The various references cited herein provide helpful background information on preparing polymers similar to the inventive compounds described herein or relevant intermediates, as well as information on formulation, uses, and administration of the polyketals of the invention, which may be of interest.

Moreover, the practitioner is directed to the specific guidance and examples provided in this document relating to various exemplary polyketals and intermediates thereof.

The polyketals of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive polyketals or compositions including them. For example, a variety of solution phase synthetic methods such as those discussed in detail below may be used. Alternatively or additionally, the inventive polyketals may be prepared using any of a variety combinatorial techniques, parallel synthesis and/or solid phase synthetic methods known in the art.

It will be appreciated as described below, that a variety of inventive polyketals can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; Larock 1990, "Comprehensive Organic Transformations: A Guide to Functional Group Preparations", $2^{nd}$ ed. VCH Publishers; and other references more specifically drawn to polymer chemistry. The methods described below are merely illustrative of some methods by which the polyketals of this invention can be synthesized, and various modifications to these methods can be made and will be suggested to a person of ordinary skill in the art having regard to this disclosure.

The starting materials, intermediates, and polyketals of this invention may be isolated and purified using conventional techniques, including filtration, distillation, crystallization, chromatography, and the like. They may be characterized using conventional methods, including physical constants and spectral data.

Example 1

Formation of Polyaldehydketal by Inulin Oxidation

Inulin from Chicory (polymerization degree ca. 35), 0.5 g was dissolved in 10 mL water at 60° C. The solution was cooled to room temperature and mixed with a suspension of 0.8 g sodium periodate in 2 mL of water. After overnight incubation, the reaction mixture was filtered and studied by size exclusion HPLC. It was found that periodate oxidation results in a small shift of the molecular weight distribution towards lower molecular weights.

Example 2

Formation of Polyalcohol Polyketal by Polyaldehydroketal Reduction

The reaction mixture of Example 1 was cooled to 0° C. (ice-bath), and was slowly poured into a cold solution of 1 g sodium borohydride in 2 ml water under stirring. The reaction mixture was kept on ice bath to prevent the temperature from rising above 20° C.

Figure 2:
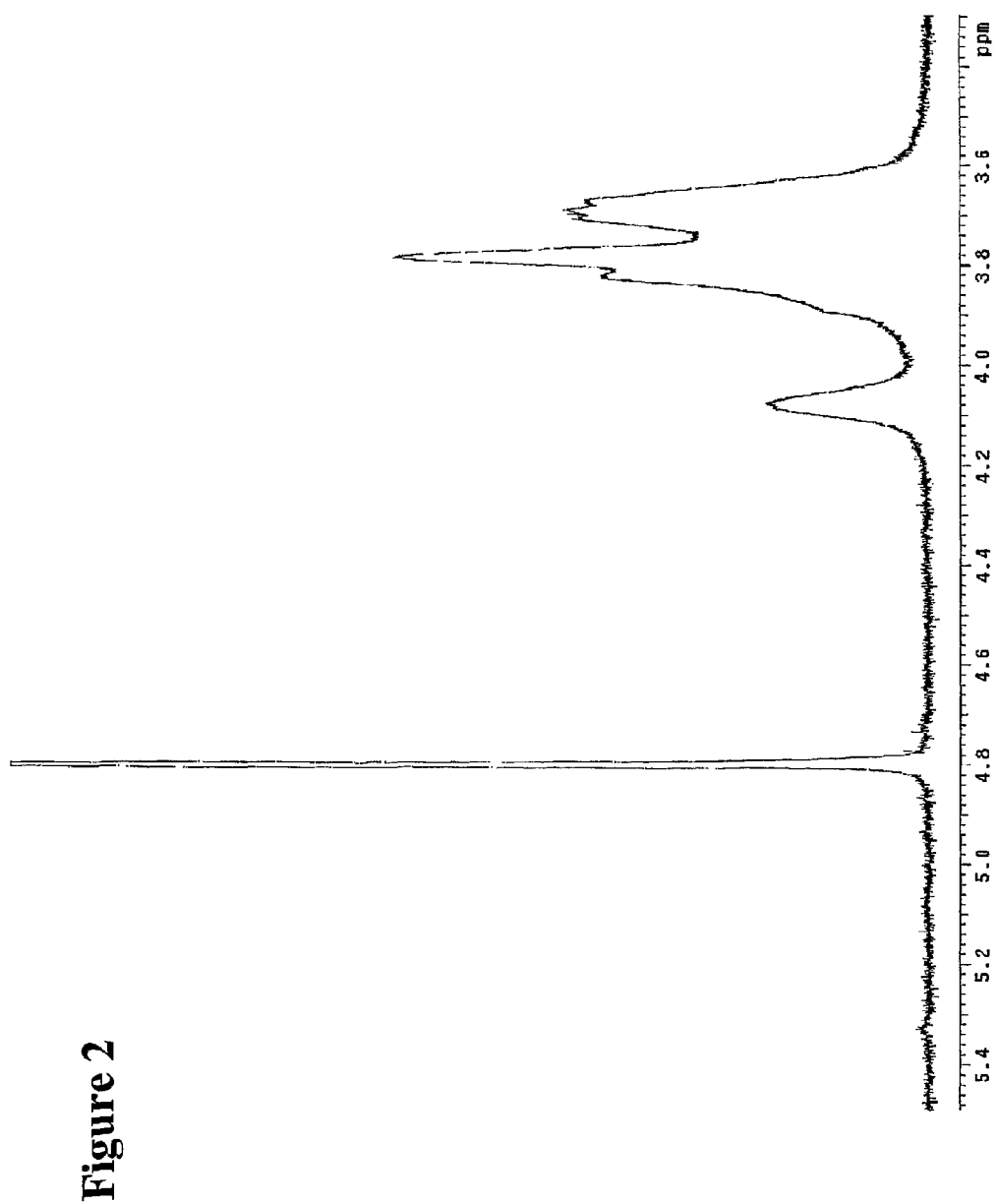
FIG. 2 depicts the proton NMR spectrum of the reaction mixture obtained in Example 2, containing poly[1-hydroxymethyl-1-(2-hydroxy-1-hydroxymethyl-ethoxy)-ethylene oxide] (e.g., PHMHO), the product of oxidative cleavage/reduction of inulin.

The reaction mixture was studied by size exclusion HPLC. Borohydride reduction was not found to further affect the apparent molecular weight distribution (FIG. 1). The product was further isolated by gel chromatography on Sephadex G-25 and lyophilized. The purified product was then studied by proton NMR spectroscopy. The obtained spectrum (FIG. 2) fully corresponded to the expected structure of poly[1-hydroxymethyl-1-(2-hydroxy-1-hydroxymethyl-ethoxy)-ethylene oxide], or PHMHO:

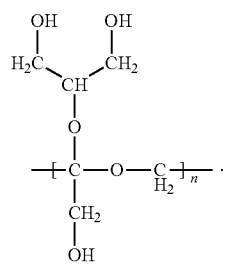

Example 3

Oxidation of Levan

Levan (purchased from Sigma-Aldrich), 0.5 g was suspended in 10 mL water at 90° C. The solution was cooled to room temperature and mixed with a suspension of 0.9 g sodium periodate in 2 mL of water. After overnight incubation on a shaker, the reaction mixture was filtered and studied by size exclusion HPLC. It was found that periodate oxidation results in shift of the molecular weight distribution towards approximately twice lower molecular weights than of original Levan.

Example 4

Reduction of Levan

The reaction mixture of Example 3 was cooled to 0° C. (ice-bath), and was slowly poured into a cold solution of 1 g sodium borohydride in 2 ml water under stirring. The reaction mixture was kept on ice bath to prevent the temperature from rising above 20° C.

Figure 3:
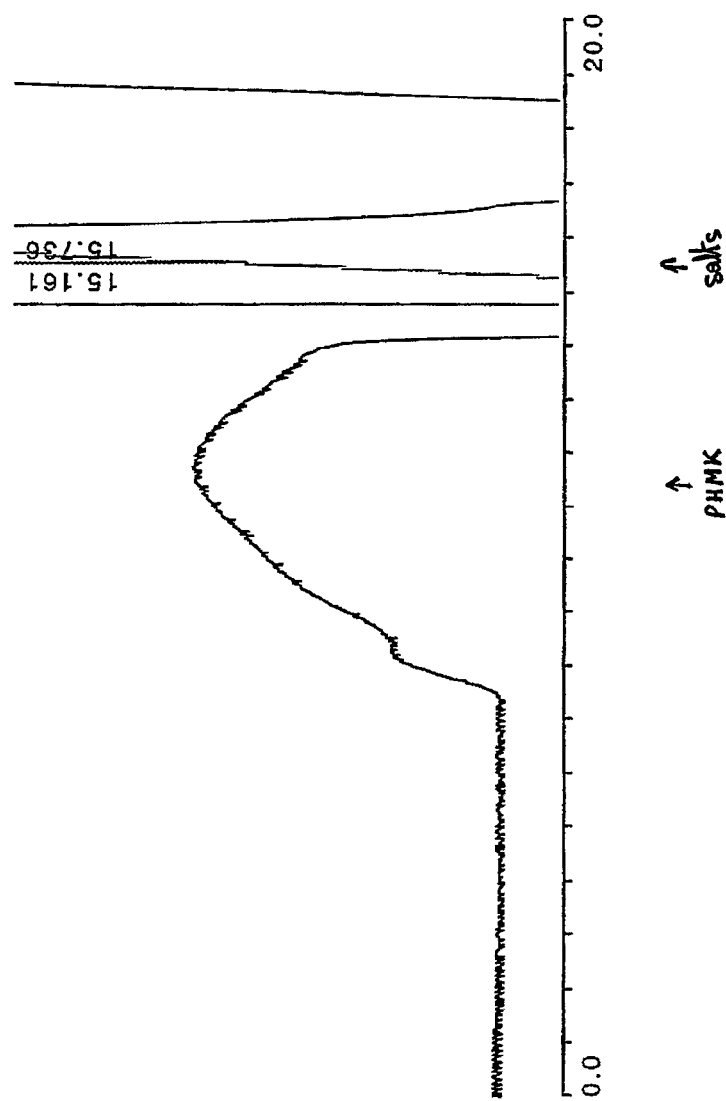
FIG. 3 depicts the size exclusion chromatogram of the reaction mixture obtained in Example 4, containing poly(hydroxymethylethylene di(hydroxymethyl)ketal) (e.g., PHMK), the product of oxidative cleavage/reduction of levan. Detection: refraction index. Column: BioRad BioSil SEC 125. Eluent: water, 0.9% NaCl. Apparent MW: 3 to 200 kDa (90% of material).
Figure 4:
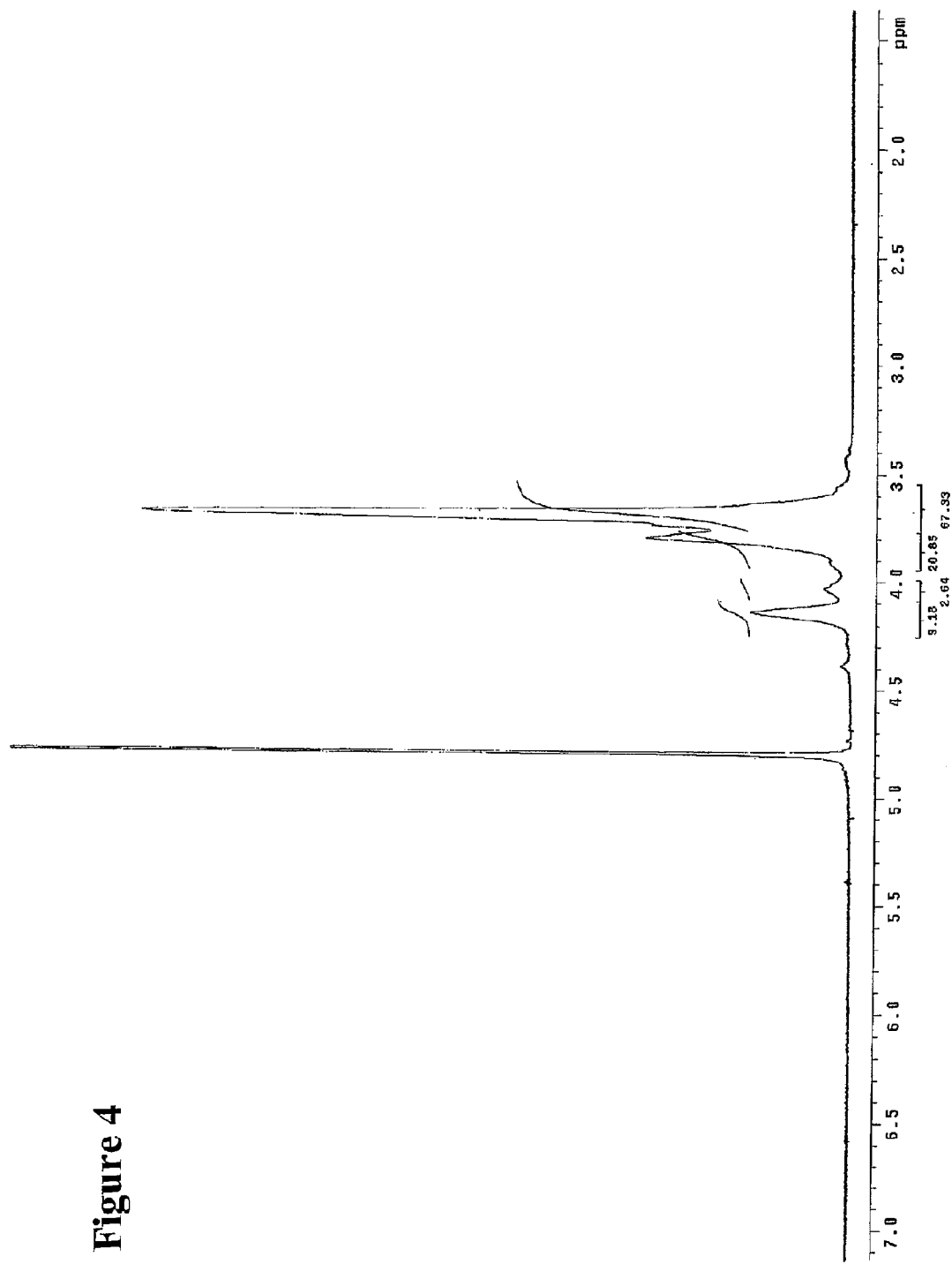
FIG. 4: depicts the proton NMR spectrum of the reaction mixture obtained in Example 4, containing poly(hydroxymethylethylene di(hydroxymethyl)ketal) (e.g., PHMK), the product of oxidative cleavage/reduction of levan.

The reaction mixture was studied by size exclusion HPLC. Borohydride reduction was found to have no effect on the apparent molecular weight distribution (FIG. 3). The product was further isolated by gel chromatography on Sephadex G-25 and lyophilized. The purified product was studied by proton NMR spectroscopy. The obtained spectrum (FIG. 4) fully corresponded to the expected structure of poly(hydroxymethylethylene di(hydroxymethyl)ketal), or PHMK:

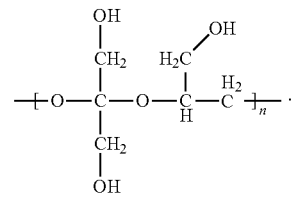

Example 5

Modification of Polyketal with Succinic Anhydride

PHMK (Example 4), 10 mg, and succinic anhydride, 2 mg, and pyridine, 5 μl, were dissolved in 100 μl DMSO. After overnight incubation, the reaction mixture was diluted with water to 1 ml and desalted by gel filtration on Sephadex G-25. The resultant polymer, succinyl-PHMK, was lyophilized.

Example 6

Modification of Succinylated Polyketal with Trypsin

Succinyl-PHMK (Example 5), 2 mg, and trypsin, 1 mg, were dissolved in 50 µl $H_2O$, N-Ethyl-N'-diethylaminopropylcarbodiimide (EDC), 2 mg, was dissolved in 50 µl of 50 mM phosphate buffer solution, pH=6.5, and added to the solution of Succinyl-PHMK and trypsin. After a 60 min incubation, the resultant conjugate of Succinyl-PHMK and trypsin was separated from the unbound trypsin by size exclusion HPLC equipped with refraction index and UV (260 nm) detectors.

Example 7

Modification of Oxidized Inulin with Doxorubicin

Oxidized inulin (polyaldehydroketal of Example 1) was prepared as described above and desalted by gel chromatography on Sephadex G-25. 1 ml of a 40 mg/ml solution of the polyaldehydroketal were mixed with 1 ml of 5 mg/ml solution of doxorubicin. Sodium cyanoborohydride (50 mg) was added to the solution, and the pH of the reaction mixture was adjusted to 7 with 1 M NaOH. After a 180 min incubation, the conjugate was separated from the unbound doxorubicine by gel filtration and lyophilized. Doxorubicine content was determined photometrically and was found to be 0.11 mg/mg of dry substance.

Example 8

Cross-Linking of Levan Polymer

PHMK (Example 4), 100 mg, and NaOH, 20 mg, were dissolved in 200 µl $H_2O$. Epichlorohydrin, 20 µl, was added under stirring. The mixture was incubated on a shaker for 5 hours. Then, the reaction mixture was heated in a boiling water bath for 1 hour. The resultant gel was extracted from the reactor, washed with water, and dried in absolute ethanol.

Example 9

Inulin-Lipid Conjugate

Random Point Modification

Oxidized inulin was prepared as described in example 1, except that periodate concentration was reduced 5-fold. Oxidized inulin was desalted by gel chromatography on Sephadex G-25. 1 ml of a 40 mg/ml solution of the oxidized inulin containing 10 mg of sodium cyanoborohydride was mixed with 0.25 ml of 10 mg/ml solution of distearoylphosphatidylethanolamine (DSPE) in methanol. The pH of the reaction mixture was adjusted to 8 with 1 M NaOH. After a 48 hr incubation on a shaker, the reaction mixture was filtered through a 0.22 µm membrane filter, and the product was purified by gel chromatography on Sephadex G-25. and lyophilized. After lyophilization, the product was washed with chloroform and dried in vacuum. The effective size of micelles formed by the product in water, as determined by SEC HPLC, was more than 15 nm.

Example 10

Transformation of Inulin-Lipid Conjugate into Polyketal-Lipid Conjugate

Inulin-DSPE conjugate of Example 8, 10 mg, was suspended in water, 100 µl. Then, 20 mg of sodium periodate were added under stirring, and the reaction mixture was incubated for 5 hours. After the incubation, the solution was mixed with 1 ml of 10% solution of sodium borohydride. After 60 min. incubation, the reaction mixture was neutralized with HCl, ant the product was purified by gel chromatography and lyophilized.

Example 11

Polyketal Conjugation with DTPA

PHMK (Example 4), 10 mg, and dicycloanhydride of diethylenetriaminepentaacetic acid (DTPA-CA), 1 mg, were dissolved in 100 µl DMF. 0.1 mg of tosylsulfonic acid were added as catalyst. After an overnight incubation, the reaction mixture was diluted with water to 1 ml and desalted by gel filtration on Sephadex G-25. The resultant polymer, DTPA-PHMK, was lyophilized.

Example 12

Polyketal-DTPA Conjugate Labeling with In-111

1 mg of DTPA-PHMK of Example 10 were dissolved in 100 µl water and mixed with solution of [$^{111}$In]Cl, 156 µCi, in 50 µl 0.5 N sodium citrate buffer, pH=5.6. After 30 min. incubation, the radiolabeled polymer was separated by gel chromatography on Sephadex G-25 and analyzed by size exclusion HPLC. The radiochemical purity was found to be >98%; activity of polymer-bound Indium-111: 97 µCi.

Example 13

Administration of Labeled Polyketal into Rat and Model Diagnostic Procedure

The radiolabeled DTPA-PHMK of Example 11, 37 µCi, was injected through the tail vein into a 360 g normal male Sprague-Dawley CD rat anesthetised with sodium pentobarbital and positioned on gamma camera for dynamic image acquisition. Image acquisition protocol (16 images, 60 sec. each) was activated simultaneously with polymer injection. The process of biodistribution of the radiolabeled polyketal was observed on the screen of the gamma camera and recorded (16 images, 60 sec. each). Images showed that, during the first 16 min. after injection, the polymer was circulating in blood with slow renal filtration.

Example 14

Acute Toxicity of PHMHO

PHMHO was dissolved in 0.9% NaCl (100 mg/ml) and injected intravenously into 6 mice at 100 mg/kg body weight. Animals were observed for 30 days after the injection. All animals survived; none showed any detectable signs of toxicity.

What is claimed is:

1. A biodegradable biocompatible acyclic polyketal comprising repeat structural units, wherein substantially all the structural units comprise:
   a) at least one ketal group wherein at least one ketal oxygen atom is within the polymer main chain, wherein the ketal group is acyclic; and
   b) at least one hydrophilic group or pharmaceutically useful group,
   wherein the biodegradable biocompatible acyclic polyketal is associated with a macromolecule.

2. The biodegradable biocompatible acyclic polyketal of claim 1, wherein at least a subset of the structural units have the structure:

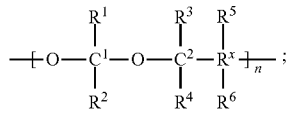

wherein each occurrence of $R^1$ and $R^2$ is independently a biocompatible group and includes a carbon atom covalently attached to $C^1$;
each occurrence of $R^x$ is a carbon atom covalently attached to $C^2$;
n is an integer;
each occurrence of $R^3$, $R^4$, $R^5$ and $R^6$ is a biocompatible group and is independently hydrogen or an organic moiety; and
for each occurrence of the bracketed structure n, at least one of $R^1$, $R^2$, $R^3$, $R^4$, $R^5$ and $R^6$ is a hydrophilic group or a pharmaceutically useful group.

3. The biodegradable biocompatible acyclic polyketal of claim 1, wherein at least a subset of the structural units have the structure:

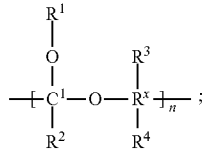

wherein each occurrence of $R^1$ is a biocompatible group;
each occurrence of $R^2$ is a biocompatible group and includes a carbon atom covalently attached to $C^1$;
each occurrence of $R^x$ is a carbon atom covalently attached to $-C^1-O-$;
n is an integer;
each occurrence of $R^1$, $R^3$ and $R^4$ is a biocompatible group and is independently hydrogen or an organic moiety; and
for each occurrence of the bracketed structure n, at least one of $R^1$, $R^2$, $R^3$, and $R^4$ is a hydrophilic group or a pharmaceutically useful group.

4. The biodegradable biocompatible acyclic polyketal of claim 1, wherein the macromolecule is a nucleic acid.

5. The biodegradable biocompatible acyclic polyketal of claim 4, wherein the macromolecule is DNA.

6. The biodegradable biocompatible acyclic polyketal of claim 4, wherein the macromolecule is RNA.

7. The biodegradable biocompatible acyclic polyketal of claim 1, wherein the macromolecule is a protein or peptide.

8. The biodegradable biocompatible acyclic polyketal of claim 7, wherein the macromolecule is an enzyme.

9. The biodegradable biocompatible acyclic polyketal of claim 4, wherein the association between the biodegradable biocompatible polyketal and nucleic acid is covalent.

10. The biodegradable biocompatible acyclic polyketal of claim 4, wherein the association between the biodegradable biocompatible polyketal and nucleic acid is non-covalent.

11. The biodegradable biocompatible acyclic polyketal of claim 10, wherein the association between the biodegradable biocompatible polyketal and nucleic acid is selected from hydrogen bonding, van der Waals interactions, hydrophobic interactions, magnetic interactions, electrostatic interactions, or a combination thereof.

12. The biodegradable biocompatible acyclic polyketal of claim 11, wherein the association between the biodegradable biocompatible polyketal and nucleic acid is electrostatic.

* * * * *